US006291639B1

(12) United States Patent
Conrad et al.

(10) Patent No.: US 6,291,639 B1
(45) Date of Patent: Sep. 18, 2001

(54) METAL-BINDING CYSTEIN-FREE PEPTIDES FOR DIAGNOSTIC AND THERAPEUTICAL PURPOSES, METHODS FOR THEIR PRODUCTION, AND PHARMACEUTICALS CONTAINING THESE COMPOUNDS

(75) Inventors: Jurgen Conrad; Ludger Dinkelborg, both of Berlin; Sebastian Erber, Ergolding; Cornelius Frommel, Zeuthen; Wolfgang Hohne, Berlin; Wolfgang Kramp, Berlin; Gabriele Kuttner, Berlin; Reinhard Malin, Berlin; Hans Martin Schier, Strausberg; Jens Schneider-Mergener; Renate Steinbrecher, both of Berlin, all of (DE)

(73) Assignee: Institut Fue Diagnostikforschung GmbH, Berlin (DE)

( * ) Notice: Subject to any disclaimer, the term of this patent is extended or adjusted under 35 U.S.C. 154(b) by 0 days.

(21) Appl. No.: 08/635,928

(22) PCT Filed: Oct. 27, 1994

(86) PCT No.: PCT/DE94/01302

§ 371 Date: Sep. 20, 1996

§ 102(e) Date: Sep. 20, 1996

(87) PCT Pub. No.: WO95/12613

PCT Pub. Date: May 11, 1995

(30) Foreign Application Priority Data

Nov. 1, 1993 (DE) ................................................ 43 37 599

(51) Int. Cl.[7] ........................... A61K 38/04; A61K 39/00
(52) U.S. Cl. ...................... 530/329; 530/328; 530/326; 530/327; 530/333; 530/391.7; 424/184.1; 424/178.1; 424/9.1
(58) Field of Search ...................................... 530/300, 326, 530/327, 328, 329, 333, 391.7; 424/9.1, 184.1, 178.1

(56) References Cited

U.S. PATENT DOCUMENTS 4,348,376 * 9/1982 Goldenberg ............................... 421/1
5,196,404 * 3/1993 Maraganore et al. .
5,639,860 * 6/1997 Tanaka et al. ....................... 530/326

FOREIGN PATENT DOCUMENTS

90/15818 * 12/1990 (WO).
91/17173 * 11/1991 (WO).
93/10747 * 10/1993 (WO).

OTHER PUBLICATIONS

Burgess et al. J. Cell Biol. 11: 2129–2138, 1990.*
Lazar et al. Mol. Cell Biol. 8: 1247–1252, 1988.*
Tao et al. J. Immunol. 143(8): 2595–2601, 1989.*
Gillies et al. Hu. Antibodies & Hybridomas 1(1): 47–54, 1990.*
Osband, ME et al. Immunol. Today 11: 193–195, 1990.*
Frank, R. Tetrahedron 48(42): 9217–9232, 1992.*

* cited by examiner

Primary Examiner—Toni R. Scheiner
(74) Attorney, Agent, or Firm—Webb Ziesenheim Logsdon Orkin & Hanson, P.C.

(57) ABSTRACT

These invention relates to metal-complexing, cysteine-free peptides which may be coupled to an organ-specific probe directly or via a linker and are thus enriched as conjugates specifically in tumors, organs, tissues or centers of inflammation. The organ-specific probes used are, for example, antibodies or part-sequences of antibodies against tumor-associated antigens, e.g. the carcino-embryonal antigen (CEA, which are thus specifically enriched in tumors. The invention also relates to processes for producing the metal-complexing cysteine-free peptides and their conjugates. The present invention also relates to the use of the conjugates as components of a kit for in vivo diagnosis or in vivo therapy and radio-pharmaceuticals containing these conjugates together with radio-isotopes. The organ-specific conjugates are used to image tumors, organs or centers of inflammation.

54 Claims, 5 Drawing Sheets

Figure 1

Figure 2:
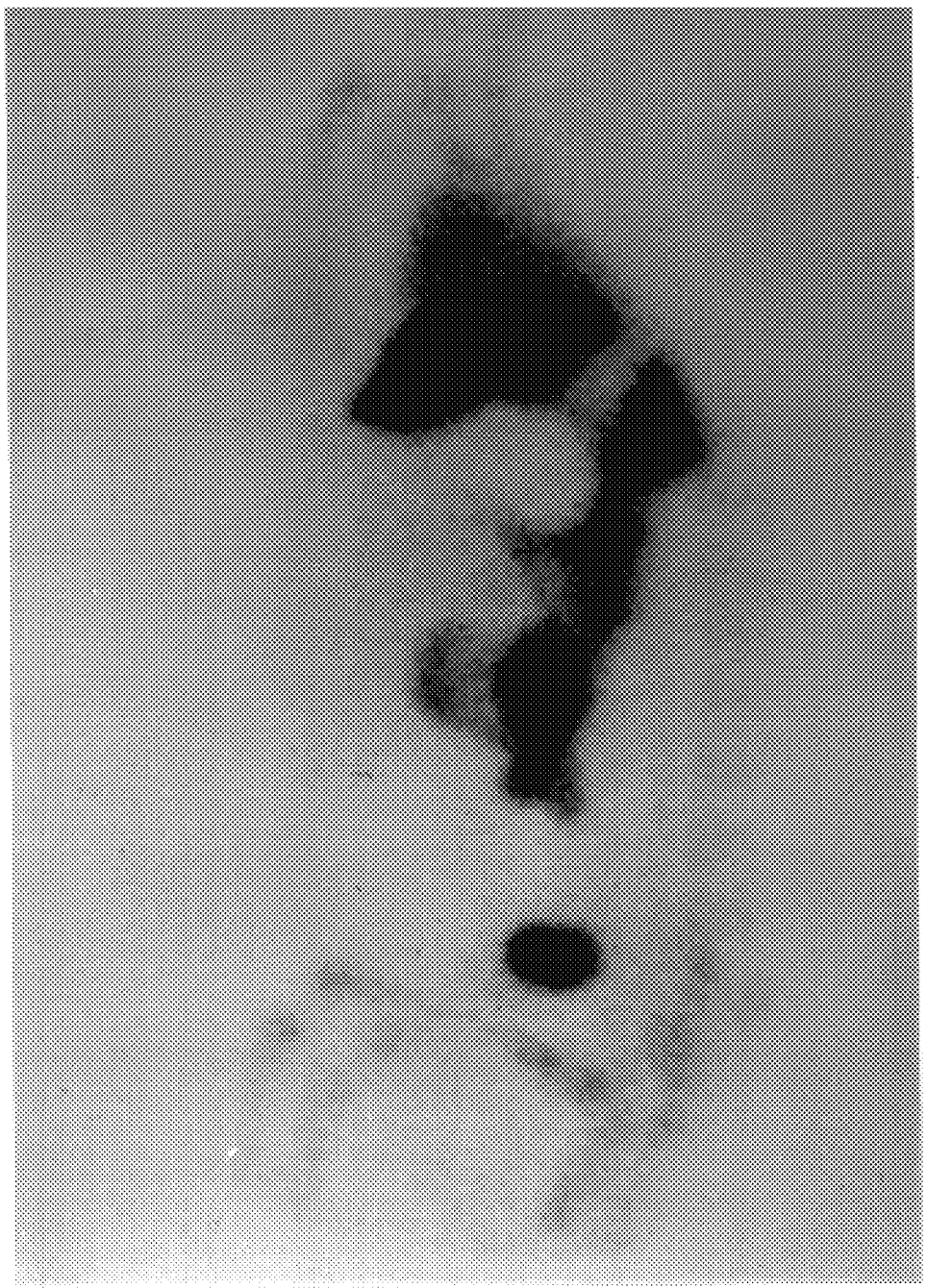

```
              10                  20                  30                  40
               |                   |                   |                   |
ACT AGT CGA CAT GGC TTG GGT GTG GAA CTG CTA TTC CTG ATG GCA
 T   S   R   H   G   L   G   V   E   L   L   F   L   M   A 50                  60                  70                  80                  90
               |                   |                   |                   |                   |
GCT GCC CAA AGT GTC CAA GCA CAG ATC CAG TTG GTG CAG TCT GGA
 A   A   Q   S   V   Q   A   Q   I   Q   L   V   Q   S   G 100                 110                 120                 130
                        |                   |                   |                   |
CCT TAC CTG AAG AAG CCT GGA GAG ACT GTC AAG ATC TCC TGC AAG
 P   Y   L   K   K   P   G   E   T   V   K   I   S   C   K 140                 150                 160                 170                 180
              |                   |                   |                   |                   |
GCT TCT GGA TAT ACC TTC ACA TAC TAT GGA ATG AAC TGG GTG AAG
 A   S   G   Y   T   F   T   Y   Y   G   M   N   W   V   K 190                 200                 210                 220
                       |                   |                   |                   |
CAG GCT CCA GGA AGG GGT TTA AAG TGG ATG GGC TTG ATA AAC ACC
 Q   A   P   G   R   G   L   K   W   M   G   L   I   N   T 230                 240                 250                 260                 270
              |                   |                   |                   |                   |
TAC ACT GGA GAG CCA ACA TAT GAT GAT GAC TTC ACG GGA CGG TTT
 Y   T   G   E   P   T   Y   D   D   D   F   T   G   R   F 280                 290                 300                 310
                       |                   |                   |                   |
GCC TTC TCT TTG GAA ACC TCT GTC AGT ACT GCC TAT TTG CAG ATC
 A   F   S   L   E   T   S   V   S   T   A   Y   L   Q   I 320                 330                 340                 350                 360
              |                   |                   |                   |                   |
AGC AAC CTC AAG AAT GAG GAC ACG GCT ACA TAT TTC TGT TCA AGA
 S   N   L   K   N   E   D   T   A   T   Y   F   C   S   R
```

```
            370             380             390             400
             |               |               |               |
GGG GGG GGT CAG GAC AGG GGT TTT GAC TAC TGG GGC CAA GGC ACC
 G   G   G   Q   D   R   G   F   D   Y   W   G   Q   G   T 410             420             430             440             450
     |               |               |               |               |
ACT CTC ACA GTC TCC TCA GGA GGC GGT GGC TCG GGA GGT GGC GGC
 T   L   T   V   S   S   G   G   G   G   S   G   G   G   G 460             470             480             490
             |               |               |               |
TCG GGT GGC GGC GGC TCT GAC ATT CAG CTG ACC CAG TCT CCA GCA
 S   G   G   G   G   S   D   I   Q   L   T   Q   S   P   A 500             510             520             530             540
     |               |               |               |               |
ATC ATG TCT GCA TCT CCA GGG GAG AAG GTC ACC ATG ACC TGC AGT
 I   M̲   S   A   S   P   G   E   K   V   T   M̲   T   C   S 550             560             570             580
             |               |               |               |
GCC AGC TCA AGT GTA AGT TAC ATG CAC TGG TAC CAG CAG AAG TCA
 A   S   S   S   V   S   Y   M̲   H   W   Y   Q   Q   K   S 590             600             610             620             630
     |               |               |               |               |
GGC ACC TCC CCC AAA AGA TGG ATT TAT GAC ACA TCC AAA CTG GCT
 G   T   S   P   K   R   W   I   Y   D   T   S   K   L   A 640             650             660             670
             |               |               |               |
TCT GGA GTC CCT GCT CGC TTC AGT GGC AGT GGG TCT GGG ACC TCT
 S   G   V   P   A   R   F   S   G   S   G   S   G   T   S 680             690             700             710             720
     |               |               |               |               |
TAC TCT CTC ACA ATC AGC ACC ATG GAG GCT GAA GAT GCT GCC ACT
 Y   S   L   T   I   S   T   M̲   E   A   E   D   A   A   T
```

```
              730             740             750             760
               |               |               |               |
TAT TAC TGC CAG CAG TGG ACT AAT AAC CCG TAC ACG TTC GGA GGG
 Y   Y   C   Q   Q   W   T   N   N   P   Y   T   F   G   G 770             780
       |               |
GGG ACC AAG CTG GAG CTG AAA
 G   T   K   L   E   L   K
```

METAL-BINDING CYSTEIN-FREE PEPTIDES FOR DIAGNOSTIC AND THERAPEUTICAL PURPOSES, METHODS FOR THEIR PRODUCTION, AND PHARMACEUTICALS CONTAINING THESE COMPOUNDS

DESCRIPTION

The object of this invention are metal-complexing, cysteine-free peptides that may be coupled, either directly or through a linker, with an organ-specific probe, and thus accumulate specifically as a conjugate in tumours, organs, tissues, or focuses of inflammation, said organ-specific probes being, for example, antibodies or partial antibody sequences used against tumour-related antigens such as the carcinoembryonal antigen (CIA), which thus accumulate specifically in tumours.

This invention further relates to methods for producing the metal-complexing cysteine-free peptides as well as their conjugates. The present invention further relates to the use of said conjugates as ingredients of a kit for in-vivo diagnostics or in-vivo therapy, and radio-pharmaceuticals that contain said conjugates and radionuclides. The organ-specific conjugates are used for the visualization of tumours, organs, or focuses of inflammation.

Apart from cardiovascular diseases, malignant carcinomas are a frequent cause of death due to their uncontrolled growth; even if the primary tumour has been removed, metastases that may be very small cannot be localized and thus not be removed. Therapeutical checks after operations or chemotherapy include, on the one hand, imaging methods such as CT or MR, on the other, determination of the content of tumour-related antigens such as CEA in the patient's serum, especially with colorectal tumours.

It is a disadvantage of these imaging methods that they cannot distinguish between the cicatrix and local recurrence. Where the CEA content in the serum is determined, the disadvantage, besides lacking tumour localization, is low sensitivity. On the one hand, formation of metastases cannot be excluded even with CEA values in the normal range, on the other hand non-malignant diseases such as inflammatory processes may result in increased CEA values.

Therefore early localization of tumours, or a tumour-specific treatment, could be decisive for the success of a therapy, especially when the diagnosis is not safe. This specific approach is facilitated by immuno-scintigraphy, an imaging method applied in nuclear medicine that is characterized by using isotope-labelled antibodies or antibody structures.

The radionuclides that are most frequently used in nuclear-medical diagnostics today are I-131, I-123, In-111 and Tc-99m; they exist in covalent bonding (I-131, I-123) or as a complex compound (In-111, Tc-99m). Although the radionuclides listed here minimize exposure of the patient to radiation due to their low half-lives, I-131, I-123 and In-111 have several disadvantages. Thus I-131, having a γ-energy of 364 keV and a half-life of 8 d, emanates additional β-radiation which is highly tissue-damaging. Studies by various research teams on In-111 having γ-energies of 172 keV and 245 keV and a half-life of 2.8 d, proved that organ-specific substances labelled with In-111 result in high concentrations in the reticuloendothelial system, especially in the liver, which makes hepatic diagnostics difficult if not impossible (Fairweather et al., Br. Med. J., 287, 167–170, 1983; Hnatowich et al., J. Nucl. Med., 26, 849–858, 1985). With its half-life of 13.3 h and γ-energy of 159 keV, the radionuclide I-123 may be well-suited for medical imaging for diagnostic purposes; its manufacture, however, is costly.

The best choice for diagnostics is Tc-99m which combines a short half-life of 6 h and a radiation energy of 140 keV that is favourable for in-vivo imaging with ready availability as it can easily and cost-effectively be gained in the form of pertechnetate by means of a molybdenum generator and is available, following reduction, at an oxidation number suited for complexing organ-specific substances.

Metals can be complexed directly or indirectly with organ-specific substances.

With direct complexing, functional groups that are contained per se in the organ-specific compound or must be represented by reduction function as ligands for Tc-99m (Schwarz et al., J. Nucl. Med., 28, 721, 1987). Antibodies may thus complex metals following reduction of the disulfide bridges but the need for reduction entails multiple disadvantages. Toxic substances such as mercaptoethanol or dithiotreitol are used as reductants and have to be separated by expensive cleaning processes after the reduction. Quite frequently, the antibody is proved to be fragmented due to the reduction, which can cause loss of antibody affinity for the target tissue in the same way as structural changes due to metal complexing can. In addition, no statement can be made about the exact location of the metal bonding position so that there can be no variation of the groups involved in complex formation, e.g. with a view to optimizing in-vivo stability.

The indirect complexing method uses bifunctional chelates such as DTPA derivatives which, following activation, can either be coupled covalently with organ-specific carriers such as antibodies, or complexed with metals (Meares, Nucl. Med. Biol., 13, 311–318, 1986).

There are basically two ways for conjugate complexing. First, the organ-specific substance is primarily coupled with the free ligand and then complexed with the radionuclide, second, the organ-specific substance is coupled with the chelate complex already formed.

Chemical coupling of the bifunctional chelates with an organ-specific substance requires in both cases sophisticated protective envelope technology as well as cleaning of the complexed conjugate.

Furthermore, protein derivation of the organ-specific substance with a bifunctional chelating agent may impair the specific bonding to the target tissue due to molecular interaction.

In-vivo localization of tumours using isotope-labelled murine antibodies against tumour-related antigens has various disadvantages. Molecular weight is a parameter for biodistribution. There is an inhomogeneous distribution combined with slow blood clearance due to high molecular weight (150 kDalton), in particular, with solid tumours. The result is high background activity which impedes optimum visualization and, together with a high concentration of antibodies in the liver, makes tumour localization difficult if not impossible (Baum et al, Nucl. Med. Commun., 10, 345–352, 1989).

Moreover, many patients show an allergic reaction by forming human antibodies against murine antibodies (HAMA reaction), which prohibits repeated use of said antibodies for diagnostic or therapeutical purposes (Sears et al., J. Biol. Resp. Modifiers, 3, 138–150, 1984). This allergic reaction is attributed to the constant antibody regions: any development to reduce the HAMA reaction is the production of chimeric antibodies having a variable antigen-detecting region of murine origin and a constant region of human origin (LoBuglio et al., Proc. Natl. Acid. Sci. USA, 86, 4220–4224, 1989).

Molecular weight can be reduced by forming antibody fragments such as F(ab)$_2$ (100 kDalton) and F(ab) (50 kDalton) to retain affinity and increase blood clearance speed (Andrew et al., Eur. J. Nucl. Med., 12, 168–172, 1986), the antibody fragments showing the disadvantages mentioned above as regards isotope labelling. Further reduction of the molecular weight is achieved by visualizing "single chain fragments" (sFv). "Single-chain fragments" have a molecular weight of 27 kDalton and consist of the variable region of the light antibody chain that is coupled through a linker with the variable region of the heavy antibody chain (Bird et al., Science, 242, 423–426, 1988).

Milenic et al. (Cancer Res., 51, 6363–6371, 1991) gave a comparative description of affinity, specificity and biodistribution of a iodinated monoclonal antibody against the tumour-related antigen TAG-72 and the respective F(ab)$_2$, F(ab) and sFv fragments. The sFv fragment shows pharmacokinetics suited for diagnostic imaging due to its lower molecular weight. The lower affinity of the monovalent sFv fragment if compared with the complete antibody is thus confronted with its much faster clearance from the blood or body which reduces background activity and results in improved imaging contrast. But the sFv fragment could not be labelled with Tc-99m, the radionuclide that is best suited for diagnostics.

According to WO 92/13527, S-protected cysteine residues interrupted by an amino acid act as Tc-99m-bonding peptides tides that are to facilitate accumulation and localization by being coupled with organ-specific polypeptides. A disadvantage of this method is the time-consuming and costly manufacture of the Tc-bonding peptides or of the conjugates, as labelling high-cysteine sequences requires sophisticated technic with respect to protecting groups.

WO-A-9015818 describes RGD sequences as receptor specific substances which are coupled with Tc-binding structures comprise cystein residues for coupling. Furthermore, RGD sequences are described, which comprise no cystein and bind Tc.

According to WO-A-9117173 a biologically active amino acid sequence is described, which is coupled with a Tc-binding amino acid sequence. These Tc-binding amino acid sequences comprise cystein or as cystein-free sequences no arg, met, lys and asn.

In WO-A-9310747 Tc-binding peptides are described, which react simultaneously as biologically active amino acid sequences. These Tc-binding peptides can comprise cystein or can be free of cystein.

Tetrahedron (1992), 48 (42), 9217–32 describes a method for the production of amino acid sequences on a membrane.

Nedelmann et al. (J. Nucl. Med., 34, 234–241, 1993) describe infarct imaging based on an animal model using a "single chain fragment" directed against myosin which is coupled with a Tc-99m-complexing bifunctional chelating agent. Cost-efficient production and easy clinical handling are impossible due to the expensive coupling of the chelating agent with the sFv fragment and the protective group technology required to prevent oxidation.

It is an urgent diagnostic and therapeutical requirement to provide compounds that stand out due to their accumulation behaviour in the target tissue and, at the same time, due to quick clearance of the portion that is not specifically bound so that they do not cause any allergenic reaction in a patient and bind radionuclides as defined and with high in-vivo stability.

Furthermore, manufacture of these compounds should be unproblematic, and their clinical handling time-saving and easy.

This problem is solved by the invention in that it provides compounds of the general formula I, $$R^1-X-R^2 \qquad (I)$$

wherein X is a chain of 20 α-, β- and/or γ-amino acid residues, same or different, said chain containing at least one amino acid belonging to the methionine, arginine, lysine and asparagine group and not containing cysteine, and having at its N-terminal either a free valency or a residue $R^1$ bonded to it by replacing a hydrogen atom, and having at its C-terminal either a free valency or a residue $R^2$ bonded to it by replacing a hydroxy group, where $R^1$ is a hydrogen atom, a branched or straight-chain alkyl, aryl, alkyl aryl, aralkyl, alkyl carbonyl or aryl carbonyl group containing up to 10 carbon atoms, that are optionally substituted by a hydroxy, amino or carboxy group, $R^2$ is a hydroxy group, a branched or straight-chain alkoxy or aryloxy group containing up to 10 carbon atoms which are optionally each substituted by a hydroxy, amino or carboxy group, an amino group, an $N(R^aR^b)$ group, where $R^a$ and $R^b$ are same or different and represent branched alkyl or acyl residues containing up to 10 carbon atoms which are optionally substituted by a hydroxy, amino or carboxy group, or is a phosphoric acid residue, their conjugates with peptides, proteins, bio- or macromolecules as well as their complexes with metal ions and their hydrosoluble salts.

Preferred are compounds according to the invention of the general formula I in which chain X consists of 3 to 15 amino acids.

Compounds in which chain X consists of 3 to 8 amino acids are particularly preferred.

Preferred are, in particular, compounds of the invention that comprise the following sequences:

glu-met-gly-asn-gly-glu,
gly-gly-gly-gly-gly-met,
met-gly-gly-gly-gly-met,
met-gly-met-gly-his-gly-his,
met-gly-met-gly-met-gly-met-gly,
gly-gly-met-gly-met-gly-gly-gly,
arg-gly-met-gly-met-gly-gly-gly,
arg-gly-met-gly-met-gly,
arg-arg-gly-gly-gly-glu,
arg-gly-gly-gly-gly-gly,
met-gly-met-gly-his-gly,
ala-lys-his-lys-his-his,
gly-met-arg-met-gly-arg,
gly-met-lys-met-gly-arg,
gly-gly-met-arg-met-gly-gly-gly or
gly-gly-met-lys-met-gly-gly-gly.

Other preferred compounds according to the invention of the general formula I $$R^1-X-R^2 \qquad (I)$$

are characterized in that $R^1$ is a single bond or a hydrogen atom, or that $R^2$ is a single bond, a hydroxy group or an amino group.

The invention further provides conjugates of peptides, proteins, bio- or macromolecules and substances bonding to receptors with compounds of the general formula I.

Conjugates are preferred in which the peptides, proteins, bio- or macromolecules and substances bonding to receptors are characterized by the fact that the conjugates are present with substances that accumulate selectively in diseased tissue or tumours, with a covalent bonding existing between said substances and compounds of the general formula I, said bonding being amidic for substances containing amino groups such as peptides, proteins, antibodies or their fragments, ester-like, and imidic for substances containing aldehyde groups.

The substances accumulating in diseased tissue are preferably hormones, neurohormones, neurotransmitters, growth-stimulating factors, vegetable hormones, pheromones, enzyme cofactors, enzyme substrates, pharmaceuticals specifically bonding to receptors, or oligonucleotides.

Particularly preferred among substances accumulating in diseased tissue are oxytocines, vasopressines, angiotensines, melanocyte-stimulating hormones, somatostatines, tyrotropin-releasing hormones, gonadotropinreleasing hormones, testosterones, estradiols, progesterones, cortisols, aldosterones, vitamin D, gastrins, secretins, somatropins, prostaglandins, neurotensins, insulins, glucagons, calcitonins, growth-hormone-releasing hormones, prolactins, encephalins, endorphins, dopamines, norepinephrines, glutamates, serotonins, acetylcholines, epinephrines, interleucines, angiogenins, thymopoetins, erythropoietins, zeatins, gibberelic acid derivatives, yeast factors, insect pheromones, coenzyme A, fibrinogens, angiotensinogens, mecamylamine, ranitidin, cimetidin, lovastatine or isoproterenol derivatives.

Other compounds of the invention are characterized in that the substances accumulating in diseased tissue or in tumours are peptides or proteins, especially antibodies, antibody fragments such as F(ab)$_2$, F(ab), single-chain antibodies or CDRs.

Particularly preferred compounds are characterized in that the antibody that accumulates in diseased tissue or in tumours is an α-CEA antibody the hybrid cell clone of which that is used for its production being deposited with the Central Institute of Molecular Biology, registration number B4-F/C3 (1988 list), or whose F(ab)$_2$, F(ab), is sFv fragments or CDRs. See FIG. 1 for the base and amino acid sequence of the variable region of the light chain and the variable region of the heavy chain of the antibody produced by the hybrid cell clone no. B4-F/C3 that are coupled via a synthetic linker.

Furthermore, compounds according to the invention are characterized in that the substances that accumulate in diseased tissue are peptides such as endothelines, partial endotheline sequences, endotheline analogues, endotheline derivatives, or endotheline antagonists.

In particular, compounds according to the invention are characterized in that the peptides comprise the following sequences:

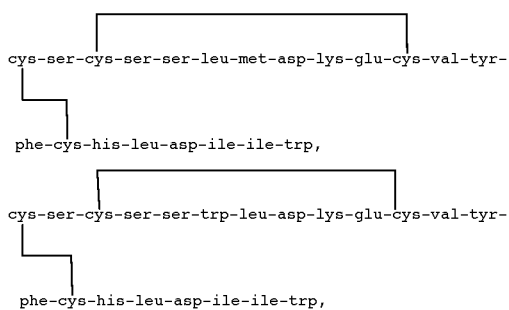

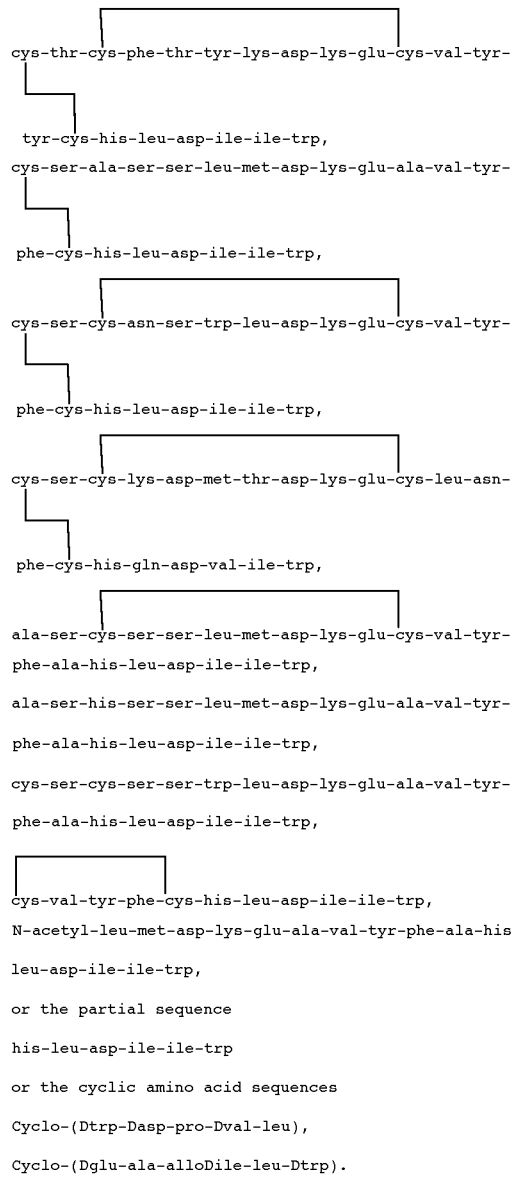

The compounds according to the invention may be present as complexes with metal ions. Preferred are complexes in which the metal ion is a radionuclide. Preferred radionuclides are isotopes of the elements Tc, Re, At, In or Ga. The radionuclide Tc-99m is particularly preferred.

Another object of the present invention is a method for the production of the compounds according to the invention of the general formula I, $$R^1—X—R^2 \qquad (I)$$

wherein X is a chain of 20 α-, β- and/or γ-amino acid residues, same or different, said chain containing at least one amino acid belonging to the methionine, arginine, lysine and asparagine groups and not containing cysteine, and having at its N-terminal either a free valency or a residue $R^1$ bonded to it by replacing a hydrogen atom, and having at its C-terminal either a free valency or a residue $R^2$ bonded to it by replacing a hydroxy group, where $R^1$ is a hydrogen atom, a branched or straight-chain alkyl, aryl, alkyl aryl, aralkyl, alkyl carbonyl or aryl carbonyl group containing up to 10 carbon atoms, that are optionally substituted by a hydroxy, amino or carboxy group, $R^2$ is a hydroxy group, a branched or straight-chain alkoxy or aryloxy group containing up to 10 carbon atoms which are optionally each substituted by a hydroxy, amino or carboxy group, an amino group, an $N(R^a R^b)$ group, where $R^a$ and $R^b$ are same or different and represent branched alkyl or acyl residues containing up to 10 carbon atoms which are optionally substituted by a hydroxy, amino or carboxy group, or is a phosphoric acid residue, their conjugates with peptides, proteins, bio- or macromolecules as well as their complexes with metal ions.

The method according to the invention is characterized in that a) amino acids are amidically coupled in the desired order, one after the other, in a generally known way, with amino acids that are coupled with synthetic resin; and that said amino acids are separated from the synthetic resin after the peptide synthesis is finished, or that b) coding oligo- or polynucleotides for the compounds of the general formula (I) are produced is by known methods of chemical synthesis of these compounds, either by linking the hydroxyl group at C-5' of a nucleotide with the phosphate group of another nucleotide or by detecting the coding mRNA strings using labelled oligonucleotides, isolating said mRNA, subsequent transformation in cDNA as well as its amplification by means of a polymerase chain reaction, placed in a customary expression vector and expressed in prokaryontic or eukaryontic cells, and that the compounds produced in this way are optionally conjugated with substances that accumulate selectively in diseased tissue or in tumours, with a covalent bonding existing between said substances that is amidic for substances containing amino groups such as peptides, proteins, antibodies or their fragments, ester-like, and imidic for substances containing aldehyde groups, and that the compounds and conjugates produced in this way are optionally reacted with a metal in the form of a salt optionally in the presence of a reductant or auxiliary ligand.

Another object of the present invention is a kit for manufacturing radiopharmaceuticals consisting of a compound of the general formula I or a conjugate of said compound with peptides, proteins, bio- or macromolecules as well as receptor-bonding substances and optionally a reductant and an auxiliary ligand, either dry or in solution, and instructions for use, including instructions for reacting the compounds described with Tc-99m or Re in the form of a pertechnetate or perrhenate solution.

Another object of the present invention are radiopharmaceutical preparations for radiotherapy and radiodiagnostics, characterized in that they contain a compound according to the invention as defined above.

The radiopharmaceutical preparations may contain the common galenic auxiliary and supporting substances and/or have the form of liposomes.

There are many advantages to using a cysteine-free peptide for complexing metals.

Thus the peptides of the invention can be produced and coupled with organ-specific probes without costly protective group technology and taking as little time as possible.

Antibodies or partial antibody sequences, peptide structures such as endothelines, endotheline derivatives, partial endotheline sequences, endotheline analogues, or endotheline antagonists, hormones, neurohormones, neurotransmitters, growth-stimulating factors, vegetable hormones, pheromones, enzyme cofactors, enzyme substrates, pharmaceuticals specifically bonding to receptors, or oligonucleotides may be used as organspecific probes.

Compounds selected from the groups mentioned above may be, for example, oxytocines, vasopressines, angiotensines, melanocyte-stimulating hormones, somatostatines, tyrotropin-releasing hormones, gonadotropinreleasing hormones, testosterones, estradiols, progesterones, cortisols, aldosterones, vitamin D, gastrins, secretins, somatropins, prostaglandins, neurotensins, insulins, glucagons, calcitonins, growth-hormonereleasing hormones, prolactins, encephalins, endorphins, dopamines, norepinephrines, glutamates, serotonins, acetylcholines, epinephrines, interleucines, angiogenins, thymopoetins, erythropoietins, zeatins, gibberelic acid derivatives, yeast factors, insect pheromones, coenzyme A, fibrinogens, angiotensinogens, mecamylamine, ranitidin, cimetidin, lovastatine or isoproterenol derivatives.

The conjugates consisting of the peptides according to the invention and the organ-specific probe may also be isolated as a whole in terms of genetic engineering.

Furthermore, a metal-complexing bonding position may be generated in the organ-specific probe. First, the three-dimensional arrangement of the amino acid sequence of an organ-specific probe such as an antibody is determined. Taking into account atomic radii and bond angles, potential bonding positions are located using mathematical and geometrical methods such as differential geometry.

At these potential bonding positions, nucleotides that do not code too well, or not at all, for metal-complexing amino acids can be replaced by nucleotides that code for metal-complexing amino acids by directing mutagenesis at them.

Generation of a metal-complexing site may include replacement of one or several amino acids, said amino acids involved in metal complexing being interrupted by one or several "loops" formed by amino acids that are not involved in metal-complexing. The metal-complexing site is generated according to known methods of molecular biology as, for example, double-string plasmid-DNA mutagenesis using T4 polymerase and selection primer (Deng et al., Anal. Bioch., 200, 81–88, 192) or double string plasmid-DNA mutagenesis using PCR (Landt et al., Gene, 96, 125–128, 1990). The organ-specific probe manipulated and modified in this way may subsequently be expressed using genetic engineering techniques.

Biomolecules per se can be modified in such a way by this method that they are characterized, while retaining their biological properties such as identification of, and bonding to, tumours, organs, tissues or focuses of inflammation, in that they are capable, in addition, of stably binding metals. Thus areas are generated in said biomolecules that correspond to the general formula I, with residues $R^1$ and $R^2$ being formed by the respective segments of the appropriately modified biomolecules.

Moreover, site-directed mutagenesis can change the biomolecules so that several areas of the general formula I are formed in a biomolecule. Complexing then generates metal complexes in which coordination positions are provided by different segments or sections of the biomolecules; the individual coordination positions may be interrupted by arbitrary amino acid chains or other spacers. It is important at any rate that the original properties of the biomolecules are retained, in particular, their capability of functioning as an organ-specific probe.

The peptides of the invention have a defined metal bonding position and show outstanding metal-complexing properties. The peptides of the invention are characterized by high in-vivo stability.

Table 1 lists the data on Tc-peptide complex stability in bovine plasma determined according to Example 5. The Tc complexes remain stable for 4 hours. This is sufficient time for therapy and diagnosis using the compounds according to the invention.

TABLE 1

Tc-peptide complex stability in bovine plasma

| Tc-Complex | stability in % after | | | protein bonding |
|---|---|---|---|---|
| | 1 h | 2 h | 4 h | in % |
| met-gly-met-gly-his-gly-his | 100 | 100 | 100 | 36.5 ± 3.6 |
| arg-gly-met-gly-met-gly-gly-gly | 95.7 | 94.6 | 92.8 | 21.0 ± 0.9 |
| arg-gly-met-gly-met-gly | 97.7 | 97.9 | 97.1 | 24.6 ± 1.7 |

It was found that conjugates consisting, for example, of partial antibody sequences against CEA and the peptides of the invention, can be expressed using genetic engineering techniques while retaining their immunogenicity as the formation of undesirable disulfide bridges and thus any faulty conjugate folding during expression is prevented when using cysteine-free peptides.

It was found, in particular, that a radiolabelled organ-specific probe composed of the α-CEA-antibody no. B4F/C3 described in DD-252200, or its fragments such as Fab2, Fab or sFv and a cysteine-free, Tc-99m-complexing peptide, bonds specifically and stably to tumours, with specific accumulation in the tumour taking place very rapidly.

The hybrid cell clone used for the production of the antibody was deposited with the Central Institute for Microbiology of the former GDR (list 1988), registration number B4-F/C3.

The variable region of the light chain and the variable region of the heavy chain were sequenced. The nucleotide sequence and the associated amino acid sequence of said region and the synthetic linker are shown in FIG. 1.

It has further been found that the conjugate portion present in the surplus is rapidly eliminated from the body. The high concentration of the radiolabelled conjugates facilitates very good tumour localization using a scintillation camera or another apparatus applied in nuclear medicine; imaging is characterized by an excellent signal-to-noise ratio.

Another remarkable feature of the conjugates according to the invention is that the time required for optimum tumour localization is low due to high accumulation specifically in the tumour and favourable pharmacokinetecs, which minimizes the patient's exposure, in particular, exposure to radiation.

Surprisingly, it was found that the cysteine-free metal-complexing peptides can per se be used for hepatic function diagnosis.

Tables 2, 3 and 4 show organ distribution and excretory kinetics of compounds according to the invention. The tests were made as described in Examples 2.3., 3.3. and 6.3.

A large portion of the radiation dosage is afterwards found in the liver. This effect can be utilized for examining hepatic functions.

TABLE 2

Distribution over organs and excretory kinetics of Tc-99m-arg-gly-met-gly-met-gly-gly-gly in mice

| time | 0.25 h | | 1.0 h | | 3.0 h | | 5.0 h | |
|---|---|---|---|---|---|---|---|---|
| % dose/g | %/g | ±S.D | %/g | ±S.D. | %/g | ±S.D. | %/g | ±S.D. |
| spleen | 0.63 | 0.23 | 0.30 | 0.10 | 0.33 | 0.15 | 0.30 | 0.00 |
| liver | 5.27 | 3.00 | 1.57 | 0.47 | 1.13 | 0.23 | 1.27 | 0.47 |
| kidney | 4.57 | 1.40 | 1.50 | 0.20 | 1.27 | 0.06 | 0.97 | 0.25 |
| lung | 1.20 | 0.26 | 0.50 | 0.10 | 0.30 | 0.00 | 0.20 | 0.10 |
| bones | 0.37 | 0.12 | 0.20 | 0.00 | 0.17 | 0.06 | 0.17 | 0.06 |
| heart | 0.40 | 0.10 | 0.20 | 0.00 | 0.10 | 0.00 | 0.10 | 0.00 |
| brain | 0.07 | 0.06 | 0.03 | 0.00 | 0.01 | 0.01 | 0.01 | 0.00 |
| tail | 1.87 | 0.55 | 0.30 | 0.10 | 0.20 | 0.00 | 0.13 | 0.06 |
| muscle | 0.27 | 0.12 | 0.10 | 0.00 | 0.04 | 0.00 | 0.03 | 0.01 |
| intestine + cont. | 23.03 | 3.18 | 27.17 | 3.04 | 21.00 | 4.28 | 11.37 | 12.63 |
| skin | 0.53 | 0.23 | 0.17 | 0.06 | 0.10 | 0.00 | 0.06 | 0.02 |
| blood | 1.13 | 0.23 | 0.43 | 0.06 | 0.20 | 0.00 | 0.13 | 0.06 |
| % ID | % | ±S.D | % | ±S.D. | % | ±S.D. | % | ±S.D. |
| spleen | 0.06 | 0.02 | 0.04 | 0.01 | 0.03 | 0.01 | 0.03 | 0.00 |
| liver | 6.98 | 2.60 | 2.07 | 0.43 | 1.48 | 0.16 | 1.27 | 0.29 |
| kidney | 1.53 | 0.50 | 0.47 | 0.09 | 0.42 | 0.06 | 0.26 | 0.06 |
| lung | 0.23 | 0.06 | 0.09 | 0.01 | 0.05 | 0.01 | 0.03 | 0.01 |
| bones | 0.01 | 0.00 | 0.01 | 0.00 | 0.00 | 0.00 | 0.00 | 0.00 |
| heart | 0.04 | 0.00 | 0.02 | 0.00 | 0.01 | 0.00 | 0.01 | 0.00 |
| brain | 0.02 | 0.00 | 0.01 | 0.00 | 0.01 | 0.00 | 0.00 | 0.00 |
| tail | 1.21 | 0.29 | 0.19 | 0.04 | 0.14 | 0.02 | 0.10 | 0.05 |
| muscle | 0.04 | 0.02 | 0.01 | 0.00 | 0.01 | 0.00 | 0.01 | 0.00 |
| intest. + cont. | 61.01 | 4.20 | 72.32 | 1.72 | 55.39 | 10.19 | 20.57 | 18.37 |
| skin | 2.03 | 0.78 | 0.59 | 0.05 | 0.30 | 0.05 | 0.21 | 0.05 |
| blood | 2.09 | 0.38 | 0.81 | 0.10 | 0.38 | 0.02 | 0.19 | 0.06 |

TABLE 2-continued

Distribution over organs and excretory kinetics of
Tc-99m-arg-gly-met-gly-met-gly-gly-gly in mice

| overall | % | ±S.D | % | ±S.D. | % | ±S.D. | % | ±S.D. |
|---|---|---|---|---|---|---|---|---|
| organs, residual body total: | 83.34 | 3.48 | 78.79 | 0.76 | 59.50 | 10.52 | 25.56 | 22.40 |
| urine total: | 15.04 | 1.46 | 22.11 | 1.42 | 20.93 | 1.44 | 23.50 | 2.13 |
| faeces total: | | | 0.17 | 0.22 | 22.89 | 10.69 | 52.04 | 24.24 |
| overall total | 98.37 | 2.93 | 101.08 | 1.94 | 103.32 | 0.99 | 101.64 | 0.97 |

TABLE 3

Distribution over organs and excretory kinetics of
Tc-99m-arg-gly-met-gly-met-gly in mice

| time | 0.25 h | | 1.0 h | | 3.0 h | | 5.0 h | |
|---|---|---|---|---|---|---|---|---|
| % dose/g | %/g | ±S.D | %/g | ±S.D. | %/g | ±S.D. | %/g | ±S.D. |
| spleen | 0.40 | 0.10 | 0.23 | 0.06 | 0.13 | 0.06 | 0.17 | 0.06 |
| liver | 5.07 | 1.21 | 2.13 | 1.27 | 0.70 | 0.10 | 0.63 | 0.12 |
| kidney | 2.43 | 0.51 | 0.97 | 0.12 | 0.67 | 0.12 | 0.60 | 0.00 |
| lung | 0.77 | 0.06 | 0.43 | 0.06 | 0.20 | 0.00 | 0.10 | 0.00 |
| bones | 0.30 | 0.10 | 0.13 | 0.06 | 0.10 | 0.00 | 0.10 | 0.00 |
| heart | 0.27 | 0.06 | 0.10 | 0.00 | 0.10 | 0.00 | 0.04 | 0.01 |
| brain | 0.03 | 0.00 | 0.02 | 0.00 | 0.04 | 0.05 | 0.03 | 0.03 |
| tail | 2.83 | 2.15 | 0.40 | 0.10 | 0.53 | 0.15 | 0.20 | 0.17 |
| muscle | 0.23 | 0.15 | 0.10 | 0.00 | 0.03 | 0.01 | 0.03 | 0.01 |
| intest. + cont. | 22.57 | 1.76 | 23.47 | 1.80 | 10.33 | 3.07 | 7.20 | 1.67 |
| skin | 0.37 | 0.06 | 0.10 | 0.00 | 0.10 | 0.00 | 0.04 | 0.01 |
| blood | 0.73 | 0.06 | 0.27 | 0.06 | 0.13 | 0.06 | 0.10 | 0.00 |

| % ID | % | ±S.D | % | ±S.D. | % | ±S.D. | % | ±S.D. |
|---|---|---|---|---|---|---|---|---|
| spleen | 0.04 | 0.00 | 0.03 | 0.00 | 0.02 | 0.00 | 0.02 | 0.00 |
| liver | 6.95 | 1.86 | 2.62 | 1.44 | 0.89 | 0.13 | 0.75 | 0.10 |
| kidney | 0.84 | 0.15 | 0.31 | 0.06 | 0.24 | 0.03 | 0.21 | 0.01 |
| lung | 0.16 | 0.01 | 0.08 | 0.01 | 0.03 | 0.00 | 0.03 | 0.00 |
| bones | 0.01 | 0.00 | 0.00 | 0.00 | 0.00 | 0.00 | 0.00 | 0.00 |
| heart | 0.03 | 0.00 | 0.01 | 0.00 | 0.01 | 0.00 | 0.00 | 0.00 |
| brain | 0.01 | 0.00 | 0.01 | 0.00 | 0.02 | 0.00 | 0.01 | 0.00 |
| tail | 1.84 | 1.42 | 0.26 | 0.07 | 0.35 | 0.11 | 0.12 | 0.11 |
| muscle | 0.04 | 0.03 | 0.01 | 0.00 | 0.01 | 0.00 | 0.01 | 0.00 |
| intest. + cont. | 63.11 | 0.74 | 67.20 | 4.58 | 28.36 | 7.57 | 24.08 | 4.11 |
| skin | 1.57 | 0.22 | 0.49 | 0.07 | 0.27 | 0.00 | 0.15 | 0.02 |
| blood | 1.35 | 0.18 | 0.49 | 0.06 | 0.27 | 0.05 | 0.16 | 0.04 |

| overall | % | ±S.D | % | ±S.D. | % | ±S.D. | % | ±S.D. |
|---|---|---|---|---|---|---|---|---|
| organs, residual body total: | 81.05 | 2.01 | 75.10 | 2.77 | 31.66 | 7.79 | 26.01 | 3.88 |
| urine total: | 19.18 | 0.95 | 25.57 | 0.39 | 14.51 | 6.70 | 22.14 | 8.15 |
| faeces total: | | | 0.82 | 0.65 | 52.06 | 16.40 | 48.39 | 11.20 |
| overall total | 100.22 | 2.26 | 101.49 | 2.52 | 98.23 | 5.56 | 96.54 | 0.60 |

TABLE 4

Distribution over organs and excretory kinetics of
Tc-99m-glu-met-gly-asn-gly-glu-cys-val-tyr-phe-cys—his—leu—asp-ile-ile-trp in mice

| time | 0.25 h | | 1.0 h | | 3.0 h | | 5.0 h | |
|---|---|---|---|---|---|---|---|---|
| % dose/g | %/g | ±S.D | %/g | ±S.D. | %/g | ±S.D. | %/g | ±S.D. |
| spleen | 3.27 | 0.29 | 1.50 | 0.26 | 1.90 | 0.10 | 1.83 | 0.06 |
| liver | 10.03 | 0.46 | 8.17 | 0.92 | 7.47 | 0.58 | 7.03 | 1.50 |
| kidney | 54.70 | 3.24 | 62.57 | 1.65 | 50.90 | 4.77 | 48.80 | 6.93 |
| lung | 4.93 | 0.38 | 2.83 | 0.06 | 1.93 | 0.38 | 1.20 | 0.26 |
| bones | 2.37 | 0.31 | 1.93 | 0.23 | 1.50 | 0.26 | 1.47 | 0.21 |
| heart | 2.97 | 0.42 | 1.77 | 0.23 | 1.00 | 0.17 | 0.77 | 0.06 |
| brain | 0.27 | 0.06 | 0.13 | 0.06 | 0.10 | 0.00 | 0.10 | 0.00 |
| tail | 3.30 | 0.17 | 3.37 | 0.06 | 1.83 | 0.12 | 2.83 | 2.74 |
| muscle | 0.70 | 0.00 | 0.50 | 0.00 | 0.33 | 0.12 | 0.20 | 0.00 |
| intest. + cont. | 1.73 | 0.23 | 2.33 | 0.15 | 2.70 | 0.00 | 2.50 | 0.70 |
| skin | 1.33 | 0.06 | 1.03 | 0.06 | 0.67 | 0.23 | 0.77 | 0.12 |
| blood | 8.80 | 1.39 | 3.60 | 0.17 | 1.90 | 0.35 | 1.20 | 0.10 |

| % ID | % | ±S.D | % | ±S.D. | % | ±S.D. | % | ±S.D. |
|---|---|---|---|---|---|---|---|---|
| spleen | 0.37 | 0.01 | 0.15 | 0.02 | 0.24 | 0.02 | 0.24 | 0.02 |
| liver | 17.76 | 2.38 | 14.19 | 0.83 | 13.64 | 0.85 | 11.38 | 2.10 |
| kidney | 20.85 | 0.56 | 23.21 | 1.54 | 18.65 | 1.58 | 18.30 | 1.91 |
| lung | 0.94 | 0.13 | 0.70 | 0.14 | 0.40 | 0.08 | 0.28 | 0.07 |
| bones | 0.07 | 0.01 | 0.06 | 0.00 | 0.05 | 0.00 | 0.05 | 0.00 |
| heart | 0.38 | 0.08 | 0.25 | 0.06 | 0.13 | 0.01 | 0.11 | 0.00 |
| brain | 0.13 | 0.01 | 0.07 | 0.00 | 0.04 | 0.01 | 0.03 | 0.00 |
| tail | 2.58 | 0.17 | 2.62 | 0.16 | 1.41 | 0.06 | 2.03 | 1.83 |
| muscle | 0.12 | 0.01 | 0.08 | 0.01 | 0.05 | 0.01 | 0.04 | 0.00 |
| intest. + cont. | 5.37 | 0.16 | 6.67 | 0.31 | 7.48 | 0.67 | 6.26 | 0.49 |
| skin | 5.14 | 0.54 | 3.94 | 0.11 | 2.85 | 0.36 | 2.78 | 0.48 |
| blood | 19.13 | 3.64 | 7.85 | 0.13 | 4.26 | 0.24 | 2.50 | 0.06 |

| overall | % | ±S.D | % | ±S.D. | % | ±S.D. | % | ±S.D. |
|---|---|---|---|---|---|---|---|---|
| organs, residual body total: | 81.42 | 4.77 | 69.20 | 0.73 | 57.05 | 2.34 | 50.93 | 2.43 |
| urine total: | 16.20 | 4.20 | 27.75 | 2.75 | 41.30 | 2.82 | 46.05 | 0.71 |
| faeces total: | | | 0.57 | 0.41 | 0.38 | 0.55 | 2.35 | 1.26 |
| overall total | 97.62 | 0.80 | 97.52 | 1.62 | 98.73 | 1.03 | 99.33 | 0.47 |

Furthermore, it was found that a radiolabelled organ-specific probe composed of a partial endotheline sequence and a Tc-99m-complexing peptide accumulates specifically at atherosclerotic changes of the vessels. Here again it is the conjugate that accumulates especially quickly in atherosclerotic lesions, thus enabling early and high-contrast visualization.

Figure 3:
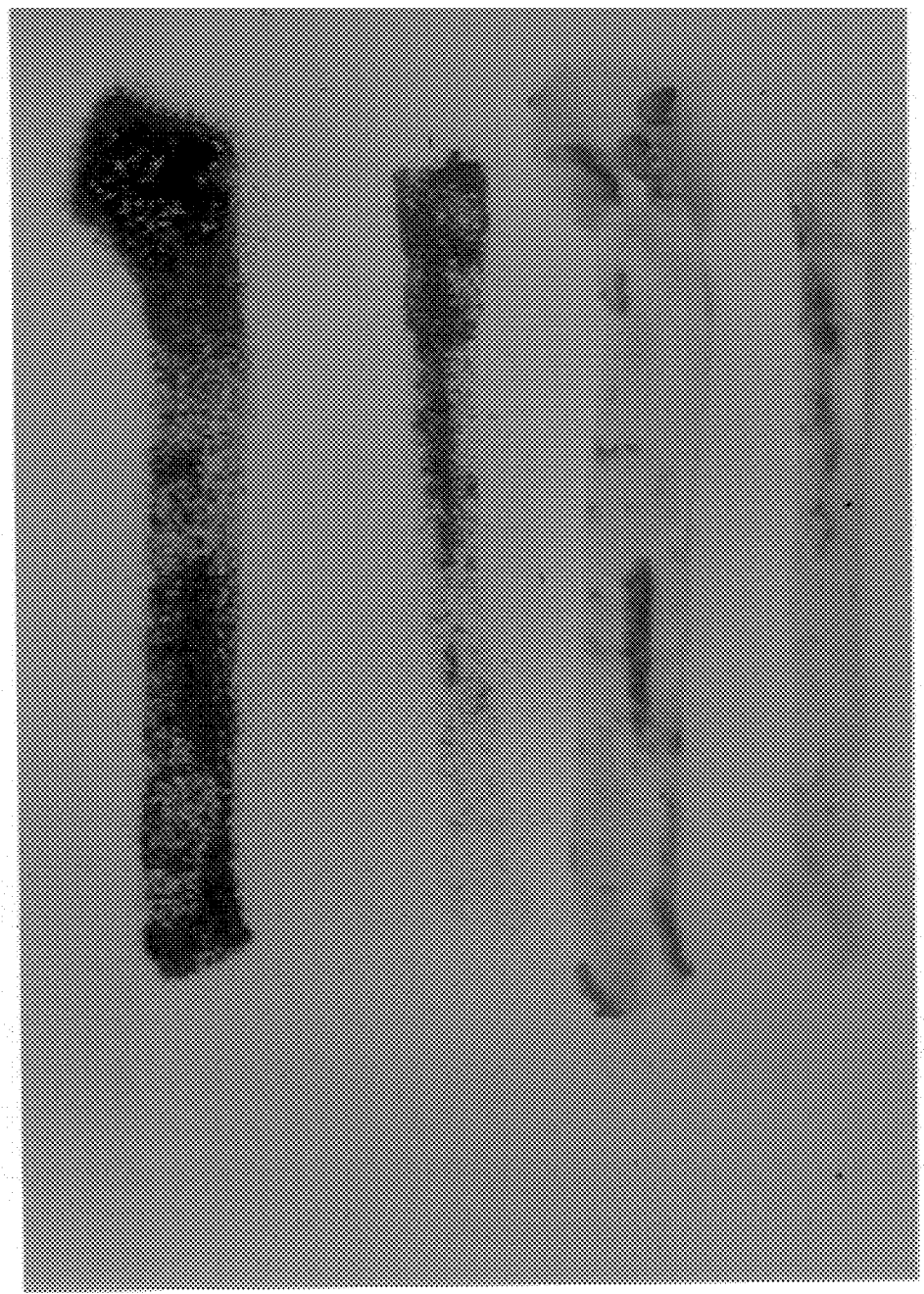

FIGS. 2 and 3 show the accumulation of the Tc-com-complexed compounds that were conjugated with the partial endotheline sequence his-leu-asp-ile-ile-trp (cf. Example 7).

The peptides of the invention and the conjugates obtained by coupling with organ-specific probes are particularly suited for use as means of diagnosis or therapy in the form of a kit.

The following examples illustrate the invention.

General Instruction for Peptide Synthesis

Fmoc-protected (9-fluorenylmethoxycarbonyl-) derivatives are preferably used as N-protected amino acids. The compounds of the general formula (I) are synthesized from the carboxy terminal to the amino terminal on synthetic resin. The compounds that are in covalent bond with the synthetic resin are separated from the synthetic resin at room temperature (2–4 h) using 97% trifluoroacetic acid/2% triisobutyl silane/1% water and cleaned by means of preparative HPLC (RP-18, gradient from 0,1% trifluoroacetic acid to 60% acetonitrile/0,1% trifluoroacetic acid within 30 minutes, at a 10 ml/min flow rate).

EXAMPLE 1

1.1) Peptides $H_2N$-met-gly-met-gly-his-gly-his-$CONH_2$ (1.1.1) $H_2N$-met-gly-met-gly-his-gly-his-COOH (1.1.2)

The peptides were synthesized and cleaned according to the above general instructions.

$C_{28}H_{44}N_{12}O_7S_2$ MW: calc. 724.8 det. 726 (FAB-MS)
$C_{28}H_{43}N_{11}O_8S_2$ MW: calc. 725.8 det. 727 (FAB-MS)

1.2) Technetium-99m Complex (1.2) of $H_2N$-met-gly-met-gly-his-gly-his-$CONH_2$ (1.2.1) or $H_2N$-met-gly-met-gly-his-gly-his-COOH (1.2.2)

A solution of 0.5 mg (0.69 μmol) $H_2N$-met-gly-met-gly-his-gly-his-$CONH_2$ or $H_2N$-met-gly-met-gly-his-gly-his-COOH in 300 μphosphate buffer ($Na_2HPO_4$, 0.5 mol/l, pH 8.5) is mixed with 50 μl of a 0.15 molar trisodium citrate dihydrate solution and 2,5 μl of a 0.2 molar tin (II) chloride dihydrate solution. After proper mixing, the reaction mixture is mixed with a pertechnetate solution (0.4–0.9 mCi) from a Mo-99/Tc-99m generator, incubated for 10 minutes at room temperature and filtered (0.2 μm filter).

Labelling is analyzed using HPLC:

MERCK nucleosile column, 125×4 mm, 5 μm; gradient from 100% A to 100% B within 7.5 min; eluent A: phosphate buffer ($Na_2HPO_4$; 0.01 M; pH 2,0); eluent B: acetonitrile/phosphate buffer ($Na_2HPO_4$; 0.01 mol; pH 2,0) 50:50 (V/V); flow rate: 1,0 ml/min. Radiochemical purity of the Tc-99m complexes is more than 95%.

EXAMPLE 2

2.1) Peptides $H_2N$-arg-gly-met-gly-met-gly-gly-gly-$CONH_2$ (2.1.1) $H_2N$-arg-gly-met-gly-met-gly-gly-gly-COOH (2.1.2)

The peptides were synthesized and cleaned according to the above general instructions.

$C_{26}H_{48}N_{12}O_8S_2$ MW: calc. 720.8 det. 722 (FAB-MS)
$C_{26}H_{47}N_{11}O_9S_2$ MW: calc. 721,8 det. 723 (FAB-MS)

2.2) Technetium-99m Complex (2.2) of $H_2N$-arg-gly-met-gly-met-gly-gly-gly-$CONH_2$ (2.2.1) or H2N-arg-gly-met-gly-met-gly-gly-gly-COOH (2.2.2)

Solutions used:

50.0 mg $SnCl_2$ dissolved in 1 ml 0.5 mol/l HCl, filled up to 10 ml with $H_2O$ bidest (22.1 mmol/l).

0.5 mol/l disodium hydrogen phosphate solution, set to pH 8.5 using NaOH (0, 1 mol/l).

500 mg of Na citrate dissolved in 10 ml $H_2O$ bidest (170 mmol/l).

10.4 mg (14.4 μmol) $H_2N$-arg-gly-met-gly-met-gly-gly-gly-$CONH_2$ or $H_2N$-arg-gly-met-gly-met-gly-gly-gly-COOH in 1 ml NaOH (1 mol/l).

100 μl Tc99m pertechnetate had an activity of 18.4 MBq (498.4 μCi).

Execution

150 μl arg-gly-met-gly-met-gly-gly-gly were mixed with 750 μl phosphate buffer, 150 μl citrate solution, 7.5 μl $SnCl_2$ and 150 μl Tc-99m pertechnetate and incubated for 20 min at room temperature. This labelling batch was then diluted with 2793 μl PBS (pH 7.4). Total volume: 4000 μl (pH 7.4) having a total activity of 6.2 MBq (168 μCi).

The Labelling was analyzed using HPLC:

MERCK nucleosile column, 125×4 mm, 5 μm; gradient from 100% A to 100% B within 7.5 min; eluent A: phosphate buffer ($Na_2HPO_4$; 0.01 mol/l; pH 2.0); eluent B: acetonitrile/phosphate buffer ($Na_2HPO_4$; 0.01 mol/l; pH 2.0) 50:50 (V/V); flow rate: 1.0 ml/min. Radiochemical yield of Tc-99m complex was 100%.

2.3) Distribution Over Organs and Elimination of the Technetium-99m Complex (2.2.1) of $H_2N$-arg-gly-met-gly-met-gly-gly-gly-$CONH_2$ Distribution over organs and excretion of Tc-99m-arg-gly-met-gly-met-gly-gly-gly (for production and labelling, see Examples 2.1.1 and 2.2.1) were examined in mice after single intravenous application.

Execution

Species: Mouse, NMRI, Schering SPF, ca. 20 g, n=12. Dosage: 100 μl per animal, corresponding to 54 nmol arg-gly-met-gly-met-gly-gly-gly having an activity of 155.4 kBq (4.2 μCi), specific activity=2.88 kBq/nmol (77.8 nCi/nmol).

Times: 0.25 h, 1 h, 3 h, 5 h after application (three animals at each time).

Parameters: Radioactivity in the blood, liver, kidneys, muscle, heart, brain, spleen, intestine, skin, lung, bones and residual body as well as in the urine and faeces.

The substance dissolved in PBS (pH 7.4) was applied to a caudal vein. The animals were kept in cages with receivers for waste products where urine and faeces were collected after application. Three animals were killed and prepared at each time indicated. Radioactivity was measured in the blood, liver, kidneys, muscle, heart, brain, spleen, intestine, skin, lung, bones and the residual body as well as in the urine and faeces using a gamma counter (program routine no. 9).

The following values were calculated: % of dose per g of tissue, % of dose in the various organs as well as in the urine and faeces (see Table 2).

EXAMPLE 3

3.1) Peptides $H_2N$-arg-gly-met-gly-met-gly-$CONH_2$ (3.1.1) $H_2N$-arg-gly-met-gly-met-gly-COOH (3.1.2)

The peptides were synthesized and cleaned according to the above general instructions.

$C_{22}H_{42}N_{10}O_6S_2$ MW: calc. 606,75 det. 605 (FAB-MS)
$C_{22}H_{41}N_9O_7S_2$ MW: calc. 607,7 det. 609 (FAB-MS)

3.2) Technetium-99m Complex [3.2] of $H_2N$-arg-gly-met-gly-met-gly-$CONH_2$ (3.2.1) or $H_2N$-arg-gly-met-gly-met-gly-COOH (3.2.2)

Solutions used 50.0 mg $SnCl_2$ dissolved in 1 ml 0.5 mol/l HCl, filled up with H20 bidest to 10 ml (22.1 mmol/l).

0.5 mol/l disodium hydrogen phosphate solution, set to pH 8.5 with NaOH (0, 1 mol/l).

500 mg Na citrate dissolved in 10 ml H20 bidest (170 mmol/l).

10.6 mg (17.5 μmol) arg-gly-met-gly-met-gly in 1 ml NaOH (1 mol/l).

100 μl Tc99m pertechnetate had an activity of 18.4 MBq (498.4 μCi).

Execution

150 µl arg-gly-met-gly-met-gly were mixed with 750 µl phosphate buffer, 150 µl citrate solution, 7.5 µl SnCl2 and 200 µl Tc-99m pertechnetate and incubated for 20 min at room temperature. The labelling batch was then diluted using 2742.5 µl PBS (pH 7.4). Total volume: 4000 µl (pH 7.4) having a total activity of 6.2 MBq (168 µCi).

The Labelling is Analyzed using HPLC:

MERCK nucleosile column, 125×4 mm, 5 µm; gradient from 100% A to 100% B within 7.5 min; eluent A: phosphate buffer (Na2HPO4; 0.01 mol/l; pH 2.0); eluent B: acetonitrile/phosphate buffer (Na2HPO4; 0.01 mol/l; pH 2.0) 50:50 (V/V); flow rate: 1.0 ml/min. The radiochemical yield of the Tc-99m complex was 100%.

3.3) Distribution Over Organs and Elimination of the Technetium-99m Complex (3.2.1) of $H_2N$-arg-gly-met-gly-met-gly-$CONH_2$ Distribution over organs and excretion of Tc-99m-arg-gly-met-gly-met-gly (for production and labelling, see Examples 3.1.1 and 3.1.2) were to be examined in mice after single intravenous application.

Execution

Species: Mouse, NMRI, Schering SPF, ca. 20 g, n=12. Dosage: 100 µl per animal, corresponding to 66 nmol arg-gly-met-gly-met-gly having an activity of 155.4 kBq (4.2 µCi), specific activity=2.37 kBq/nmol (64 nCi/nmol).

Times: 0.25 h, 1 h, 3 h, 5 h after application (three animals for each time).

Parameters: Radioactivity in the blood, liver, kidneys, muscle, heart, brain, spleen, intestine, skin, lung, bones and the residual body as well as in the urine and faeces.

The substance dissolved in PBS (pH 7.4) was applied to a caudal vein. The animals were kept in cages with receivers for waste products where urine and faeces were collected after application. Three animals were killed and prepared at each of the times given. Radioactivity was measured in the blood, liver, kidneys, muscle, heart, brain, spleen, intestine, skin, lung, bones and the residual body as well as in the urine and faeces using a gamma counter (program routine no. 9).

The following values were calculated: % of dose per g of tissue, % of dose in the various organs as well as in the urine and faeces (see Table 3).

EXAMPLE 4

4.1) H2N-glu-met-gly-asn-gly-glu-CONH2 (4.1)

The peptide was synthesized and cleaned according to the above general instructions.

$C_{23}H_{38}N_8O_{11}S$ MW: calc. 634,7 det. 636 (FAB-MS)

4.2) Technetium-99m Complex (4.2) of H2N-glu-met-gly-asn-gly-glu-CONH2

A solution of 0.5 mg (0.8 µmol) H2N-glu-met-gly-asn-gly-glu-CONH2 (4.1) in 300 µl phosphate buffer (Na2HPO4, 0.5 mol/l, pH 8,5) is mixed with 50 µl of a 0.15 molar trisodium citrate dihydrate solution and 2.5 µl of a 0.2 molar tin(II)chloride dihydrate solution. The reaction mixture is mixed with a pertechnetate solution (0.4–0.9 mCi) from a Mo-99/Tc-99m generator after thorough mixing, incubated for 10 minutes at room temperature, and the filtrated (0.2 µm filter).

The Labelling is Analyzed using HPLC:

MERCK nucleosile column, 125×4 mm, 5 µm; gradient from 100% A to 100% B within 7.5 min; eluent A: phosphate buffer (Na2HPO4; 0.01 M; pH 2,0); eluent B: acetonitrile/phosphate buffer ($Na_2HPO_4$; 0.01 mol; pH 2,0) 50:50 (V/V); flow rate: 1,0 ml/min. The radiochemical purity of the Tc-99m complex is more than 95%.

EXAMPLE 5

In-vitro Stability of the Tc-peptide Complexes

The stability of the Tc-peptide complex not bonded to protein was determined as follows: The peptides were synthesized and cleaned according to the above general instructions and labelled as described in Example 1. 0.5 ml (corresp. to 0.5 mCi) of the labelling batch were each mixed with 4.5 ml of bovine plasma (Fa. Kraeber) or PBS. A 1 ml sample is taken from each of the two batches immediately after mixing and after 1h, 2h, and 4h, and the protein is separated by ultrafiltration (Centricon 30.000 by Fa. Amicon). The filtrate is separated using HPLC: MERCK nucleosile column, 125×4 mm, 5 µm; gradient from 100% A to 100% B within 7.5 min; eluent A: phosphate buffer (Na2HPO4; 0.01 M; pH 2.0); eluent B: acetonitrile/phosphate buffer (Na2HPO4; 0.01 mol; pH 2,0) 50:50 (V/V); flow rate: 1.0 ml/min. The protein bond of the Tc-peptide complex was calculated from the peak area difference of complexes incubated with bovine plasma and with PBS. Stability was determined by taking the total of peak areas as 100% and calculating the percentage of the peak area of a complex. The peptide complexes examined remain stable for 4h (see Table 1).

EXAMPLE 6

6.1) H2N-glu-met-gly-asn-gly-glu-cys-val-tyr-phe-cys-his-leu-asp-ile-trp-COOH (6.1)

The peptide was synthesized and cleaned according to the above general instructions.

MW: calc. 2029.31 det. 2030 (FAB-MS)

6.2) Technetium-99m Complex (6.2) of H2N-glu-met-gly-asn-gly-glu-cys-val-tyr-phe-cys-his-leu-asp-ile-trp-COOH Solutions used 50 mg SnCl2 dissolved in 10 ml 0.1 mol/l HCl (22.1 mmol/l).

0.1 mol/l disodium hydrogen phosphate solution, set to pH 7.5 using NaOH (0, 1 mol/l).

Na gluconate solution (0.01 mol/l H2O bidest).

0.5 mg (0.272 µmol) H2N-glu-met-gly-asn-gly-glu-cys-val-tyr-phe-cys-his-leu-asp-ile-ile-trp-COOH dissolved in 500 µl H20 (bidest) and 100 µl phosphate buffer.

100 µl Tc99m pertechnetate had an activity of 1.8 MBq (48 µCi).

Execution

Labelling of Gluconate with Tc-99m:

2 ml Na gluconate solution are mixed with 0.5 ml of Tc-99m pertechnetate (37 MBq/1 mCi) and twice with 15 µl SnCl2. Complete labelling of the gluconate was checked using TLC, silica gel 60; eluent acetone.

Labelling of H2N-glu-met-gly-asn-gly-glu-cys-val-tyr-phe-cys-his-leu-asp-ile-ile-trp-COOH with Tc-99m Gluconate:

120 µl H2N-glu-met-gly-asn-gly-glu-cys-val-tyr-phe-cys-his-leu-asp-ile-ile-trp-COOH were mixed with 2 ml of the Tc-99m-Na gluconate solution and incubated for 15 min at room temperature. Total volume: 2120 µl (pH 7.0) having a total activity of 7.1 MBq (193.2 µCi). The The Labelling is Analyzed using HPLC:

MERCK nucleosile column, 125×4 mm, 5 µm; gradient from 100% A to 100% B within 8 min; eluent A: phosphate buffer (Na2HPO4; 0.01 M; pH 7.5); eluent B: acetonitrile/phosphate buffer (Na2HPO4; 0.01 mol/l; pH 7.5) 50:50 (V/V); flow rate: 1.0 ml/min. The radiochemical yield of Tc-99m complex was 95%.

6.3) Distribution over organs and elimination of the Technetium-99m Complex [6.2] of H2N-glu-met-gly-asn-gly-glu-cys-val-tyr-phe-cys-his-asp-ile-ile-trp-COOH Distribution over organs and excretion of Tc-99m-glu-met-gly-asn-gly-glu-cys-val-tyr-phe-cys-his-leu-asp-ile-ile-trp (for production and labelling see Examples 6.1 and 6.2) were examined in mice after single intravenous application.
Execution Species: Mouse, NMRI, Schering SPF, ca. 20 g, n=12. Dosage: 100 µl per animal, corresponding to 242 pmol glu-met-gly-asn-gly-glu-cys-val-tyr-phe-cys-his-leu-asp-ile-ile-trp having an activity of 111 kBq (3 µCi), specific activity=459 kBq/nmol (12,4 µCi/nmol). Times: 0.25 h, 1 h, 3 h, 5 h nach application (three animals for each time).

Parameters: Radioactivity in the blood, liver, kidneys, muscle, heart, brain, spleen, intestine, skin, lung, bones and the residual body as well as in the urine and faeces.

The substance dissolved in PBS (pH 7.4) was applied to a caudal vein. The animals were kept in cages with receivers for waste products where urine and faeces were collected after application. Three animals were killed and prepared at each of the times given. Radioactivity was measured in the blood, liver, kidneys, muscle, heart, brain, spleen, intestine, skin, lung, bones and the residual body as well as in the urine and faeces using a gamma counter (program routine no. 9).

The following values were calculated: % of dose per g of tissue, % of dose in the various organs as well as in the urine and faeces (see Table 4).

EXAMPLE 7

Detection of atherosclerotic vascular lesion in WHHL rabbits.

Atherosclerotic vascular lesions were visualized in WHHL rabbits with a gamma camera by means of Tc-99m-glu-met-gly-asn-gly-glu-cys-val-tyr-phe-cys-his-leu-asp-ile-ile-trp after single intravenous application. Production and labelling were carried out as described in Examples 6.1 and 6.2.
Execution Species: Froxfield rabbits HH 047560, Emsicon-Jung, female, 4.3 kg, born Oct. 15, 1992. The serum cholesterol level on May 3, 1993 was 24.6 mmol/l, Narcosis: Rompun/Ketavet (1:2), ca. 3 ml i. m. (initially), 100 µl/min i. v. Dosage: 1 ml, corresponding to 54, 3 nmol glu-met-gly-asn-gly-glu-cys-val-tyr-phe-cys-his-leu-asp-ile-ile-trp having an activity of 37 MBq (1 mCi), specific activity =681 kBq/nmol (18.4 µCi/nmol).

Recording parameters: gamma camera: Elcint SP4 HR, energy: 140 keV, rate mode: standard, collimator: 4, mode: word, frame size: 128, zoom: 1, rotation: 180°
Measuring Parameters: Relative Intensities in the Various Organs and in the Aorta Period of observation: 0–5 h after i. v. application of Tc-99m-glu-met-gly-asn-gly-glu-cys-val-tyr-phe-cys-his-leu-asp-ile-ile-trp.

Planar recordings of different length and from various positions were made over the whole test period. The rabbit was killed after 5 h using T-61 (1 ml), the aorta was removed, and a Sudan (III) dyeing and an autoradiogram (phosphorus imager) of the aorta were carried out.
Findings 1 ml of Tc-99m-glu-met-gly-asn-gly-glu-cys-val-tyr-phe-cys-his-leu-asp-ile-ile-trp was applied to the WHHL rabbit via an ear vein. WHHL rabbits show a high LDL level in the blood due to a lacking or defective LDL receptor and therefore spontaneously develop atherosclerotic vascular changes. A left lateral recording 0.5 h p.i. showed high activity in the heart, liver, kidneys and bladder and low activity in bones. The atherosclerotic lesions in the abdominal aortic area are visible (see FIG. 2).

The rabbit was killed 5 h after application, and both a Sudan (III) dyeing and an autoradiogram of the aorta were carried out (see FIG. 3). Specific activity was 353 cpm/mm$^2$ in the plaque and 42 cpm/mm$^2$ in the normal aortic wall (enrichment factor=8).

EXAMPLE 8

Single chain Fv fragment with Tc-binding peptide mRNA was isolated from a murine anti-CEA producing hybridom cell culture according to the standard protocol, and cDNA produced from it that serves as a template for a PCR with suitable primer combinations for generating the complete $V_L$ and $V_H$ coding regions of the antibody.

A synthetic oligonucleotide was used for the linker peptide that codes for (GGGGS)$_3$, and another synthetic oligonucleotide for the Tc-binding peptide (Tc peptide) that codes for the PPMGMGHG sequence. An assembling PCR according to standard protocol with TAQ polymerase resulted in a construct that codes for the $V_H$-linker-$V_L$-Tc-peptide or $V_L$-linker-$V_H$-Tc-peptide sequence.

Expression in E.coli, TG 1 strain, was carried out after cloning in a modified vector (pHEN derivative) with codification for the signal peptide of pectatelyase from Erwinia carotivorum for expression as a soluble single-chain Fv fragment in the periplasmatic space. Expression was proved by means of the western blot technique using polyclonal serum against the linker peptide or the Tc-binding peptide.

The periplasmatic fraction was gained by osmotic shock, and the soluble single-chain Fv fragment was cleaned by affinity chromatography based on antiidiotypical antibodies, antibodies directed against the linker peptide, or based on the metal ion affinity of the Tc-peptide via metal chelate columns.

EXAMPLE 9

Single-chain Fv Fragment having its Tc-bonding Position in the Framework

The construct for the single-chain Fv fragment was produced as described in Example 1 but Tc-binding variants were produced by site-related mutagenesis in the framework area of $V_L$ (loop of positions L:36 to L:43) or in the framework area of $V_H$ (loop of positions H:38 to H:45) using synthetic primers; said variants having the MGMGHG loop sequences either in the $V_H$ or $V_L$ area, or in both areas for improved Tc labelling.

We claim:
1. A compound of the general formula I,

$$R^1—X—R^2 \qquad (I)$$

wherein
X is a chain selected from the group consisting of glu-met-gly-asn-gly-glu (SEQ ID NO: 1), gly-gly-gly-gly-gly-met (SEQ ID NO: 2), met-gly-gly-gly-gly-met (SEQ ID NO: 3), met-gly-met-gly-his-gly-his (SEQ ID NO: 4), met-gly-met-gly-met-gly-met-gly (SEQ ID NO: 5), gly-gly-met-qlv-met-gly-gly-gly (SEQ ID NO: 6), arg-gly-met-gly-met-gly-gly-gly (SEQ ID NO: 7), arg-gly-met-gly-met-gly (SEQ ID NO: 8), arg-arq-gly-gly-gly-glu (SEQ ID NO: 9), met-gly-met-gly-his-gly (SEQ ID NO: 11), ala-lys-his-lys-his-his (SEQ ID NO: 12), gly-met-arg-met-gly-arg (SEQ ID NO: 13), gly-met-lys-met-gly-arg (SEQ ID NO: 14). gly-gly-met-arg-met-gly-gly-gly (SEQ ID NO: 15), gly-gly-met-lys-met-gly-gly-gly (SEQ ID NO: 16), and having at an N-terminal thereof either a free valency or a residue $R^1$-bonded to it by replacing a hydrogen atom, and having at its C-terminal either a free valency or a residue $R^2$ bonded to it by replacing a hydroxy group,
where
$R^1$ is a hydrogen atom, a branched or straight-chain alkyl, aryl, alkyl aryl, aralkyl, alkyl carbonyl or aryl carbonyl group containing up to 10 carbon atoms, that are optionally substituted by a hydroxy, amino or carboxy group,
$R^2$ is a hydroxy group, a branched or straight-chain alkoxy or aryloxy group containing up to 10 carbon atoms which are optionally each substituted by a hydroxy, amino or carboxy group, an amino group, an $N(R^aR^b)$ group,
where $R^a$ and $R^b$ are the same or different and represent branched alkyl or acyl residues containing up to 10 carbon atoms which are optionally substituted by a hydroxy, amino or carboxy group, or is a phosphoric acid residue,
their conjugates with peptides, proteins, bio- or macromolecules as well as their complexes with metal ions and their hydrosoluble salts.

2. A compound according to claim 1, wherein $R^1$ has a single bond or a hydrogen atom.

3. A compound according to claim 1, wherein $R^2$ has a single bond, a hydroxy group or amino group.

4. A compound according to claim 2, wherein $R^2$ has a single bond, a hydroxy group or amino group.

5. A compound according to claim 4, wherein the compound is conjugated to a substance that accumulates selectively in diseased tissue or tumours, with a covalent bond existing between said compound and said substance that is amidic for substances containing amino groups ester-like, and imidic for substances containing aldehyde groups.

6. A compound according to claim 5, wherein the substances accumulating in diseased tissue are hormones, neurohormones, neurotransmitters, growth-stimulating factors, vegetable hormones, pheromones, enzyme cofactors, enzyme substrates, pharmaceuticals specifically bonding to receptors, or oligonucleotides.

7. A compound according to claim 6, wherein the substances accumulating in diseased tissue are oxytocines, vasopressines, angiotensines, melanocyte-stimulating hormones, somatostatines, tyrotropin-releasing hormones, gonadotropin-releasing hormones, testosterones, estradiols, progesterones, cortisols, aldosterones, vitamin D, gastrins, secreting, somatropins, prostaglandins, neurotensins, insulins, glucagons, calcitonins, growth-hormone-releasing hormones, prolactins, encephaliins, endorphins, dopamines, norepinephrines, glutamates, serotonins, acetylcholines, epinephrines, interleucines, angiogenins, thymopoetins, erythropoietins, zeatins, gibberelic acid yeast factors, insect pheromones, coenzyme A, fibrinogens, angiotensinogens, mecamylamine, ranitidin, cimetidin, lovastatine or isoproterenols.

8. A compound according to claim 2, wherein the compound is conjugated to a substance that accumulates selectively in diseased tissue or tumours, with a covalent bond existing between said compound and said substance that is amidic for substances containing amino groups ester-like, and imidic for substances containing aldehyde groups.

9. A compound according to claim 8, wherein the substances accumulating in diseased tissue are hormones, neurohormones, neurotransmitters, growth-stimulating factors, vegetable hormones, pheromones, enzyme cofactors, enzyme substrates, pharmaceuticals specifically bonding to receptors, or oligonucleotides.

10. A compound according to claim 9, wherein the substances accumulating in diseased tissue are oxytocines, vasopressines, angiotensines, melanocyte-stimulating hormones, somatostatines, tyrotropin-releasing hormones, gonadotropin-releasing hormones, testosterones, estradiols, progesterones, cortisols, aldosterones, vitamin D, gastrins, secreting, somatropins, prostaglandins, neurotensins, insulins, glucagons, calcitonins, growth-hormone-releasing hormones, prolactins, encephalins, endorphins, dopamines, norepinephrines, glutamates, serotonins, acetylcholines, epinephrines, interleucines, angiogenins, thymopoetins, erythropoietins, zeatins, gibberelic acids, yeast factors, insect pheromones, coenzyme A, fibrinogens, angiotensinogens, mecamylamine, ranitidin, cimetidin, lovastatine or isoproterenols.

11. A compound according to claim 3, wherein the compound is conjugated to a substance that accumulates selectively in diseased tissue or tumours, with a covalent bond existing between said compound and said substance that is amidic for substances containing amino groups ester-like, and imidic for substances containing aldehyde groups.

12. A compound according to claim 11, wherein the substances accumulating in diseased tissue are hormones, neurohormones, neurotransmitters, growth-stimulating factors, vegetable hormones, pheromones, enzyme cofactors, enzyme substrates, pharmaceuticals specifically bonding to receptors, or oligonucleotides.

13. A compound according to claim 12, wherein the substances accumulating in diseased tissue are oxytocines, vasopressines, angiotensines, melanocyte-stimulating hormones, somatostatines, tyrotropin-releasing hormones, gonadotropin-releasing hormones, testosterones, estradiols, progesterones, cortisols, aldosterones, vitamin D, gastrins, secreting, somatropins, prostaglandins, neurotensins, insulins, glucagons, calcitonins, growth-hormone-releasing hormones, prolactins, encephaliins, endorphins, dopamines, norepinephrines, glutamates, serotonins, acetylcholines, epinephrines, interleucines, angiogenins, thymopoetins, erythropoietins, zeatins, gibberelic acids, yeast factors, insect pheromones, coenzyme A, fibrinogens, angiotensinogens, mecamylamine, ranitidin, cimetidin, lovastatine or isoproterenols.

14. A compound according to claim 1, wherein said compound is conjugated to a substance that accumulates selectively in diseased tissue or tumours, with a covalent bond existing between said compound and said substance that is amidic for substances containing amino groups ester-like, and imidic for substances containing aldehyde groups.

15. A compound according to claim 14, wherein the substances accumulating in diseased tissue are hormones, neurohormones, neurotransmitters, growth-stimulating factors, vegetable hormones, pheromones, enzyme cofactors, enzyme substrates, pharmaceuticals specifically bonding to receptors, or oligonucleotides.

16. A compound according to claim 15, wherein the substances accumulating in diseased tissue are oxytocines, vasopressines, angiotensines, melanocyte-stimulating hormones, somatostatines, tyrotropin-releasing hormones, gonadotropin-releasing hormones, testosterones, estradiols, progesterones, cortisols, aldosterones, vitamin D, gastrins, secreting, somatropins, prostaglandins, neurotensins, insulins, glucagons, calcitonins, growth-hormone-releasing hormones, prolactins, encephalins, endorphins, dopamines, norepinephrines, glutamates, serotonins, acetylcholines, epinephrines, interleucines, angiogenins, thymopoetins, erythropoietins, zeatins, gibberellic acids, yeast factors, insect pheromones, coenzyme A, fibrinogens, angiotensinogens, mecamylamine, ranitidin, cimetidin, lovastatine or isoproterenols.

17. A compound according to claim 5, wherein the substances accumulating in diseased tissue or in tumours are peptides, proteins, antibodies, F(ab)$_2$ fragments, F(ab) fragments, single-chain antibodies or CDRs.

18. A compound according to claim 17, wherein the antibody accumulating in diseased tissue or in tumours is an α-CEA-antibody, or its F(ab)$_2$, F(ab), sFv fragments or CDRs.

19. A compound according to claim 8, wherein the substances accumulating in diseased tissue or in tumours are peptides, proteins, antibodies, F(ab)$_2$ fragments, F(ab) fragments, single-chain antibodies or CDRs.

20. A compound according to claim 19, wherein the antibody accumulating in diseased tissue or in tumours is an α-CEA-antibody, or its F(ab)$_2$, F(ab), sFv fragments or CDRs.

21. A compound according to claim 11, wherein the substances accumulating in diseased tissue or in tumours are peptides, proteins, antibodies, F(ab)$_2$ fragments, F(ab) fragments, single-chain antibodies or CDRs.

22. A compound according to claim 21, wherein the antibody accumulating in diseased tissue or in tumours is an α-CEA-antibody, or its F(ab)$_2$, F(ab), sFv fragments or CDRs.

23. A compound according to claim 14, wherein the substances accumulating in diseased tissue or in tumours are peptides, proteins, antibodies, F(ab)$_2$ fragments, F(ab) fragments, single-chain antibodies or CDRs.

24. A compound according to claim 23, wherein the antibody accumulating in diseased tissue or in tumours is an α-CEA-antibody, or its F(ab)$_2$, F(ab), sFv fragments or CDRs.

25. A compound according to claim 5, wherein the substances accumulating in diseased tissue are peptides such as endothelines, partial endotheline sequences, endotheline analogues, or endotheline antagonists.

26. A compound according to claim 25, wherein the peptides comprise the following sequences:

```
cys-ser-cys-ser-ser-leu-met-asp-lys-glu-cys-val-tyr-
phe-cys-his-leu-asp-ile-ile-trp (SEQ ID NO: 17), cys-ser-cys-ser-ser-trp-leu-asp-lys-glu-cys-val-tyr-
phe-cys-his-leu-asp-ile-ile-trp (SEQ ID NO: 18), cys-thr-cys-phe-thr-tyr-lys-asp-lys-glu-cys-val-tyr-
tyr-cys-his-leu-asp-ile-ile-trp (SEQ ID NO: 19), cys-ser-ala-ser-ser-leu-met-asp-lys-glu-ala-val-tyr-
phe-cys-his-leu-asp-ile-ile-trp (SEQ ID NO: 20), cys-ser-cys-asn-ser-trp-leu-asp-lys-glu-cys-val-tyr-
phe-cys-his-leu-asp-ile-ile-trp (SEQ ID NO: 21), cys-ser-cys-lys-asp-met-thr-asp-lys-glu-cys-leu-asn-
phe-cys-his-gln-asp-val-ile-trp (SEQ ID NO: 22), ala-ser-cys-ser-ser-leu-met-asp-lys-glu-cys-val-tyr-
phe-ala-his-leu-asp-ile-ile-trp (SEQ ID NO: 23), ala-ser-ala-ser-ser-leu-met-asp-lys-glu-ala-val-tyr
phe-ala-his-leu-asp-ile-ile-trp (SEQ ID NO: 24), cys-ser-cys-ser-ser-trp-leu-asp-lys-glu-ala-val-tyr-
phe-ala-his-leu-asp-ile-ile-trp (SEQ ID NO: 25), cys-val-tyr-phe-cys-his-leu-asp-ile-ile-trp (SEQ ID NO:26),
N-acetyl-leu-met-asp-lys-glu-ala-val-tyr-phe-ala-
his-leu-asp-ile-ile-trp (SEQ ID NO: 27), or the partial sequence his-leu-asp-ile-ile-trp (SEQ ID NO: 28)

or the cyclic amino acid sequences

Cyclo-(Dtrp-Dasp-pro-Dval-leu),

Cyclo-Dglu-ala-alloDile-leu-Dtrp).
```

27. A compound according to claim 8, wherein the substances accumulating in diseased tissue are peptides such as endothelines, partial endotheline sequences, endotheline analogues, or endotheline antagonists.

28. A compound according to claim 27, wherein the peptides comprise the following sequences:

cys-ser-cys-ser-ser-leu-met-asp-lys-glu-cys-val-tyr-
phe-cys-his-leu-asp-ile-ile-trp (SEQ ID NO: 17),
(disulfide bond between cys1-cys3 and cys9-cys15 shown by brackets)

cys-ser-cys-ser-ser-trp-leu-asp-lys-glu-cys-val-tyr-
phe-cys-his-leu-asp-ile-ile-trp (SEQ ID NO: 18), cys-thr-cys-phe-thr-tyr-lys-asp-lys-glu-cys-val-tyr-
tyr-cys-his-leu-asp-ile-ile-trp (SEQ ID NO: 19), cys-ser-ala-ser-ser-leu-met-asp-lys-glu-ala-val-tyr-
phe-cys-his-leu-asp-ile-ile-trp (SEQ ID NO: 20), cys-ser-cys-asn-ser-trp-leu-asp-lys-glu-cys-val-tyr-
phe-cys-his-leu-asp-ile-ile-trp (SEQ ID NO: 21), cys-ser-cys-lys-asp-met-thr-asp-lys-glu-cys-leu-asn-
phe-cys-his-gln-asp-val-ile-trp (SEQ ID NO: 22), ala-ser-cys-ser-ser-leu-met-asp-lys-glu-cys-val-tyr-
phe-ala-his-leu-asp-ile-ile-trp (SEQ ID NO: 23), ala-ser-ala-ser-ser-leu-met-asp-lys-glu-ala-val-tyr-
phe-ala-his-leu-asp-ile-ile-trp (SEQ ID NO: 24), cys-ser-cys-ser-ser-trp-leu-asp-lys-glu-ala-val-tyr-
phe-ala-his-leu-asp-ile-ile-trp (SEQ ID NO: 25), cys-val-tyr-phe-cys-his-leu-asp-ile-ile-trp (SEQ ID NO:26),
N-acetyl-leu-met-asp-lys-glu-ala-val-tyr-phe-ala-
his-leu-asp-ile-ile-trp (SEQ ID NO: 27), or the partial sequence his-leu-asp-ile-ile-trp (SEQ ID NO: 28)

or the cyclic amino acid sequences

Cyclo-(Dtrp-Dasp-pro-Dval-leu),

Cyclo-Dglu-ala-alloDile-leu-Dtrp).

29. A compound according to claim 11, wherein the substances accumulating in diseased tissue are peptides such as endothelines, partial endotheline sequences, endotheline analogues, or endotheline antagonists.

30. A compound according to claim 29, wherein the peptides comprise the following sequences:

31. A compound according to claim 14, wherein the substances accumulating in diseased tissue are peptides such as endothelines, partial endotheline sequences, endotheline analogues, or endotheline antagonists.

32. A compound according to claim 31, wherein the peptides comprise the following sequences:

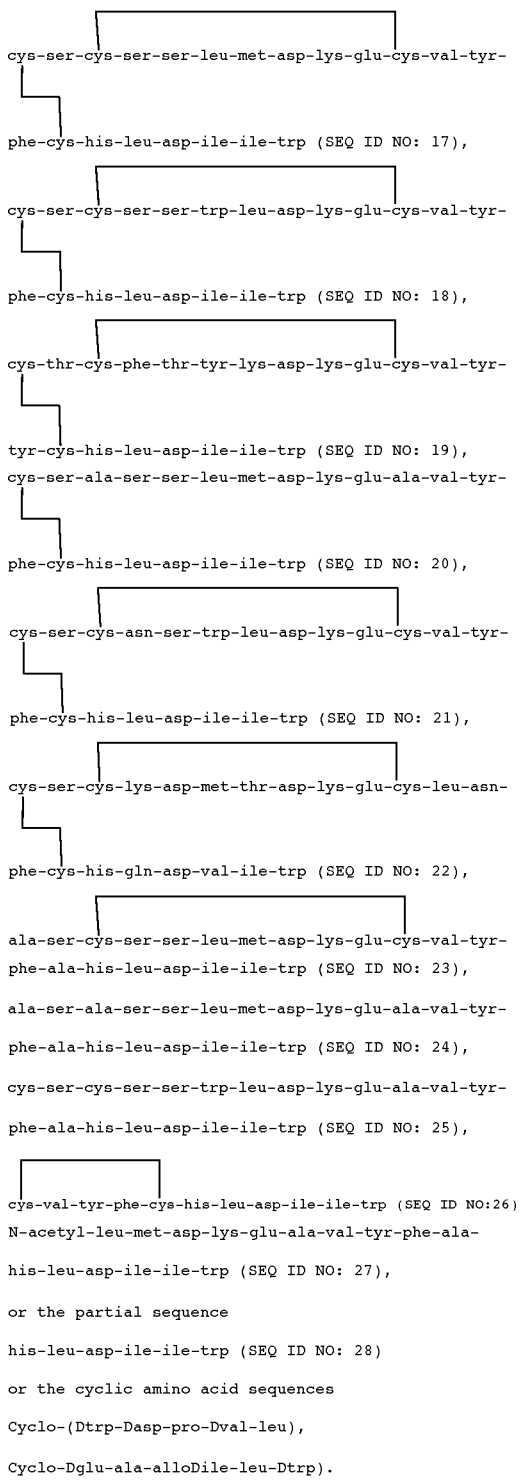

```
cys-ser-cys-ser-ser-leu-met-asp-lys-glu-cys-val-tyr-
phe-cys-his-leu-asp-ile-ile-trp (SEQ ID NO: 17), cys-ser-cys-ser-ser-trp-leu-asp-lys-glu-cys-val-tyr-
phe-cys-his-leu-asp-ile-ile-trp (SEQ ID NO: 18), cys-thr-cys-phe-thr-tyr-lys-asp-lys-glu-cys-val-tyr-
tyr-cys-his-leu-asp-ile-ile-trp (SEQ ID NO: 19),
cys-ser-ala-ser-ser-leu-met-asp-lys-glu-ala-val-tyr-
phe-cys-his-leu-asp-ile-ile-trp (SEQ ID NO: 20), cys-ser-cys-asn-ser-trp-leu-asp-lys-glu-cys-val-tyr-
phe-cys-his-leu-asp-ile-ile-trp (SEQ ID NO: 21), cys-ser-cys-lys-asp-met-thr-asp-lys-glu-cys-leu-asn-
phe-cys-his-gln-asp-val-ile-trp (SEQ ID NO: 22), ala-ser-cys-ser-ser-leu-met-asp-lys-glu-cys-val-tyr-
phe-ala-his-leu-asp-ile-ile-trp (SEQ ID NO: 23),
ala-ser-ala-ser-ser-leu-met-asp-lys-glu-ala-val-tyr-
phe-ala-his-leu-asp-ile-ile-trp (SEQ ID NO: 24),
cys-ser-cys-ser-ser-trp-leu-asp-lys-glu-ala-val-tyr-
phe-ala-his-leu-asp-ile-ile-trp (SEQ ID NO: 25), cys-val-tyr-phe-cys-his-leu-asp-ile-ile-trp (SEQ ID NO:26)
N-acetyl-leu-met-asp-lys-glu-ala-val-tyr-phe-ala-
his-leu-asp-ile-ile-trp (SEQ ID NO: 27), or the partial sequence
his-leu-asp-ile-ile-trp (SEQ ID NO: 28)
or the cyclic amino acid sequences
Cyclo-(Dtrp-Dasp-pro-Dval-leu),
Cyclo-Dglu-ala-alloDile-leu-Dtrp).
```

33. A compound according to claim 1, wherein the metal ion of the complexes is a radionuclide.

34. A compound according to claim 33, wherein the radionuclide is an isotope of the elements Tc, Re, At, In or Ga.

35. A compound according to claim 33, wherein the radionuclide is Tc-99m.

36. A compound according to claim 2, wherein the metal ion of the complexes is a radionuclide.

37. A compound according to claim 36, wherein the radionuclide is an isotope of the elements Tc, Re, At, In or Ga.

38. A compound according to claim 36, wherein the radionuclide is Tc-99m.

39. A compound according to claim 3, wherein the metal ion of the complexes is a radionuclide.

40. A compound according to claim 39, wherein the radionuclide is an isotope of the elements Tc, Re, At, In or Ga.

41. A compound according to claim 39, wherein the radionuclide is Tc-99m.

42. A compound according to claim 4, wherein the metal ion of the complexes is a radionuclide.

43. A compound according to claim 42, wherein the radionuclide is an isotope of the elements Tc, Re, At, In or Ga.

44. A compound according to claim 42, wherein the radionuclide is Tc-99m.

45. A compound according to claim 1, wherein the metal ion of the complexes is a radionuclide.

46. A compound according to claim 45, wherein the radionuclide is an isotope of the elements Tc, Re, At, In or Ga.

47. A compound according to claim 45, wherein the radionuclide is Tc-99m.

48. A compound according to claim 7, wherein the metal ion of the complexes is a radionuclide.

49. A compound according to claim 48, wherein the radionuclide is an isotope of the elements Tc, Re, At, In or Ga.

50. A compound according to claim 48, wherein the radionuclide is Tc-99m.

51. A method for manufacturing compounds of the general formula I, $$R^1\text{—}X\text{—}R^2 \qquad (I)$$

wherein

X is a chain of up to 20 α-, β- and/or γ-amino-acid residues, same or different, said chain containing at least one amino acid belonging to the methionine, arginine, lysine and asparagine group and not containing cysteine, said chain further being selected from the group consisting of glu-met-gly-asn-gly-glu (SEQ ID NO: 1), gly-gly-gly-qly-gly-met (SEQ ID NO: 2), met-gly-gly-gly-gly-met (SEQ ID NO: 3), met-gly-met-gly-his-gly-his (SEQ ID NO: 4), met-gly-met-gly-met-gly-met-gly (SEQ ID NO: 5), gly-gly-met-gly-met-gly-gly-gly (SEQ ID NO: 6), arg-gly-met-gly-met-gly-gly-gly (SEQ ID NO: 7), arg-gly-met-gly-met-gly (SEQ ID NO: 8), arg-arg-gly-gly-gly-glu (SEQ ID NO: 9), met-gly-met-gly-his-gly (SEQ ID NO: 11), ala-lys-his-lys-his-his (SEQ ID NO: 12), gly-met-arg-met-gly-arg (SEQ ID NO: 13), gly-met-lys-met-gly-arg (SEQ ID NO: 14), gly-gly-met-arg-met-gly-gly-gly (SEQ ID NO: 15), gly-gly-met-lys-met-gly-gly-gly (SEQ ID NO: 16), and having at its N-terminal either a free valency or a residue $R^1$ bonded to it by replacing a hydrogen atom, and having at its C-terminal either a free valency or a residue $R^2$ bonded to it by replacing a hydroxy group, where $R^1$ is a hydrogen atom, a branched or straight-chain alkyl, aryl, alkyl aryl, aralkyl, alkyl carbonyl or aryl carbonyl group containing up to 10 carbon atoms, that are optionally substituted by a hydroxy, amino or carboxy group, $R^2$ is a hydroxy group, a branched or straight-chain alkoxy or aryloxy group containing up to 10 carbon atoms which are optionally each substituted by a hydroxy, amino or carboxy group, an amino group, an $N(R^a R^b)$ group, where $R^a$ and $R^b$ are the same or different and represent branched alkyl or acyl residues containing up to 10 carbon atoms which may be replaced by a hydroxy, amino or carboxy group, or is a phosphoric acid residue, as well as their conjugates with peptides, proteins, bio- or macromolecules as well as their complexes with metal ions, characterized in that a) amino acids are amidically coupled in the desired order, one after the other, in a generally known way, with amino acids that are coupled with synthetic resin; and that said amino acids are separated from the synthetic resin after the peptide synthesis is finished, or that b) coding oligo- or polynucleotides for the compounds of the general formula (I) are produced by known methods of chemical synthesis of these compounds, either by linking the hydroxyl group at C-5' of a nucleotide with the phosphate group of another nucleotide or by detecting the coding mRNA strings using labelled oligonucleotides, isolating said mRNA, subsequent transformation in cDNA as well as its amplification by means of a polymerase chain reaction, placed in a customary expression vector and expressed in prokaryotic or eukaryotic cells, and that the compounds produced in this way may be conjugated, if required, with substances that accumulate selectively in diseased tissue or in tumors, with a covalent bonding existing between said substances that is amidic for substances containing amino groups such as peptides, proteins, antibodies or their fragments, ester-like, and imidic for substances containing aldehyde groups, and that the compounds and conjugates produced in this way are optionally reacted with a metal in the form of a salt, optionally in the presence of a reductant or auxiliary ligand.

52. A kit for manufacturing radiopharmaceuticals, comprising a compound according to claim 1, as well as a reductant and optionally an auxiliary ligand, either dry or in solution, and instructions for use, including instructions for reacting the compounds described with Tc-99m or Re in the form of a pertechnetate or perrhenate solution.

53. A radiopharmaceutical preparation for radiotherapy or radiodiagnostics, which contains a compound according to claim 1.

54. A radiopharmaceutical preparation according to claim 53, which contains the compound in the form of liposomes.

* * * * *

UNITED STATES PATENT AND TRADEMARK OFFICE
CERTIFICATE OF CORRECTION

PATENT NO.   : 6,291,639 B1
DATED        : September 18, 2001
INVENTOR(S)  : Jurgen Conrad et al.

It is certified that error appears in the above-identified patent and that said Letters Patent is hereby corrected as shown below:

Title Page,
Item [73], Assignee, should read: -- Institut Für Diagnostikforschung GmbH An Der Freien Universität Berlin, Berlin (DE) --.

Column 1,
Line 6, "DESCRIPTION" should read -- BACKGROUND OF THE INVENTION --.
Line 14, "(CIA)" should read -- (CEA) --.

Column 3,
Line 14, "a iodinated" should read -- an iodinated --.
Line 27, "peptides tides" should read -- peptides --.

Column 4,
Before line 1, insert: -- SUMMARY OF THE INVENTION --.
Line 1, "This problem is" should read -- The problems of the prior art are --.
Line 28, insert:
--BRIEF DESCRIPTION OF THE DRAWINGS
Fig. 1 depicts the base and amino acid sequences of the variable region of the light chain and the variable region of the heavy chain of an α-CEA antibody that accumulates in diseased tissue or in tumors; the antibody is produced from hybrid cell clone number B4-F/C3.
Fig. 2 depicts the left lateral, static recording of a WHHL rabbit which had been administered 0.5 h.p.i. of Tc-99m-glu-met-gly-asn-gly-glu-cys-val-tyr-phe-cys-his-leu-asp-ile-trp according to Example 7, showing high activity in the heart, liver, kidneys and bladder and low activity in bones; atherosclerotic lesions in the abdominal aortic area are visible.
Fig. 3 depicts a Sudan (III) dye image and an autoradiogram of the aorta of a WHHL rabbit administered 0.5 h.p.i. of Tc-99m-glu-met-gly-asn-gly-glu-cys-val-tyr-phe-cys-his-leu-asp-ile-trp according to Example 7.
DETAILED DESCRIPTION OF THE INVENTION--.

Line 36, after "glu-met-gly-asn-gly-glu" insert -- SEQ ID NO: 1 --.
Line 37, after "gly-gly-gly-gly-gly-met" insert -- SEQ ID NO: 2--.
Line 38, after "met-gly-gly-gly-gly-met" insert -- SEQ ID NO: 3--.
Line 39, after "met-gly-met-gly-his-gly-his" insert -- SEQ ID NO: 4 --.
Line 41, after "met-gly-met-gly-met-gly-met-gly" insert -- SEQ ID NO: 5 --.
Line 42, after "gly-gly-met-gly-met-gly-gly-gly" insert -- SEQ ID NO: 6 --.
Line 43, after ""arg-gly-met-gly-met-gly-gly-gly" insert -- SEQ ID NO: 7 --.
Line 44, after "arg-gly-met-gly-met-gly" insert -- SEQ ID NO: 8 --.
Line 46, after "arg-arg-gly-gly-gly-glu" insert -- SEQ ID NO: 9 --.
Line 47, after "arg-gly-gly-gly-gly-gly" insert -- SEQ ID NO: 10 --
Line 48, after "met-gly-met-gly-his-gly" insert -- SEQ ID NO: 11 --.
Line 49, after "ala-lys-his-lys-his-his" insert -- SEQ ID NO: 12 --.
Line 50, after "gly-met-arg-met-gly-art" insert -- SEQ ID NO: 13 --.
Line 51, after "gly-met-lys-met-gly-arg" insert -- SEQ ID NO: 14 --.
Line 52, after "gly-gly-met-arg-met-gly-gly-gly" insert -- SEQ ID NO: 15 --.
Line 53, after "gly-gly-met-lys-met-gly-gly-gly" insert -- SEQ ID NO: 16 --.

UNITED STATES PATENT AND TRADEMARK OFFICE
CERTIFICATE OF CORRECTION

PATENT NO. : 6,291,639 B1
DATED : September 18, 2001
INVENTOR(S) : Jurgen Conrad et al.

It is certified that error appears in the above-identified patent and that said Letters Patent is hereby corrected as shown below:

Column 5,
Line 60, after "phe-cys-his-leu-asp-ile-ile-trp," insert -- SEQ ID NO: 17 --.
Line 66, after "phe-cys-his-leu-asp-ile-ile-trp," insert -- SEQ ID NO: 18 --.

Column 6,
Line 7, after "tyr-cys-his-leu-asp-ile-ile-trp," insert -- SEQ ID NO: 19 --.
Line 11, after "phe-cys-his-leu-asp-ile-ile-trp," insert -- SEQ ID NO: 20 --.
Line 17, after "phe-cys-his-leu-asp-ile-ile-trp," insert -- SEQ ID NO: 21 --.
Line 23, after "phe-cys-his-gln-asp-val-ile-trp," insert -- SEQ ID NO: 22 --.
Line 26, after "phe-ala-his-leu-asp-ile-ile-trp," insert -- SEQ ID NO: 23 --.
Line 30, after "phe-ala-his-leu-asp-ile-ile-trp," insert -- SEQ ID NO: 24 --.
Line 33, after "phe-ale-his-leu-asp-ile-ile-trp," insert -- SEQ ID NO: 25 --.
Line 35, after "cys-val-tyr-phe-cys-his-leu-asp-ile-ile-trp," insert -- SEQ ID NO: 26 --.
Line 38, after "leu-asp-ile-ile-trp," insert -- SEQ ID NO: 27 --.
Line 41, after "his-leu-asp-ile-ile-trp," insert -- SEQ ID NO: 28 --.

Column 7,
Line 23, "produced is by" should read -- produced by --.

Column 8,
Line 46, "192)" should read -- 1992) --.

Column 9,
Table 1, Line 21, after "met-gly-met-gly-his-gly-his" insert -- SEQ ID NO: 4 --.
Table 1, Line 22, after "arg-gly-met-gly-met-gly-gly-gly" insert -- SEQ ID NO: 7 --.
Table 1, Line 23, after "arg-gly-met-gly-met-gly" insert -- SEQ ID NO: 8 --.

Column 10,
Header Table 2, after "Tc-99m-arg-gly-met-gly-met-gly-gly-gly" insert -- SEQ ID NO: 7 --.

Column 11,
Header Table 2-continued, after "Tc-99m-arg-gly-met-gly-gly-gly" insert -- SEQ ID NO: 7 --.
Line 2 of header Table 3, after "Tc-99m-arg-gly-met-gly-met-gly" insert -- SEQ ID NO: 8 --.

Column 12,
Line 3 of header Table 4, after "cys-his-leu-asp-ile-ile-trp" insert -- SEQ ID NO: 33 --.

UNITED STATES PATENT AND TRADEMARK OFFICE
CERTIFICATE OF CORRECTION

PATENT NO. : 6,291,639 B1
DATED : September 18, 2001
INVENTOR(S) : Jurgen Conrad et al.

It is certified that error appears in the above-identified patent and that said Letters Patent is hereby corrected as shown below:

Column 13,
Lines 1-2, "Tc-com-complexed" should read -- Tc-complexed --.
Line 3, after "his-leu-asp-ile-ile-trp" insert -- SEQ ID NO: 28--.
Line 22, after "(1.1.1)" insert -- SEQ ID NO: 11 --.
Line 22, after "(1.1.2)" insert -- SEQ ID NO: 11 --.
Line 28, after "(1.2.1)" insert -- SEQ ID NO: 11 --.
Line 29, after "(1.2.2)" insert -- SEQ ID NO: 11 --.
Line 31, after "$CONH_2$" insert -- SEQ ID NO: 11 --.
Line 32, after "COOH" insert -- SEQ ID NO: 11 --.
Line 49, after "(2.1.1)" insert -- SEQ ID NO: 7 --.
Line 50, after "(2.1.2)" insert -- SEQ ID NO: 7 --.
Line 56, after "(2.2.1)" insert -- SEQ ID NO: 7 --.
Line 56, "H2N" should read -- $H_2N$ --.
Line 57, after "(2.2.2)" insert -- SEQ ID NO: 7 --.
Line 66, after "$CONH_2$" insert -- SEQ ID NO: 7 --.
Line 67, after "COOH" insert -- SEQ ID NO: 7 --.

Column 14,
Line 4, after "arg-gly-met-gly-met-gly-gly-gly" insert -- SEQ ID NO: 7 --.
Line 19, after "$CONH_2$" insert -- SEQ ID NO: 7 --.
Line 21, after "gly-met-gly-met-gly-gly-gly" insert -- SEQ ID NO: 7 --.
Line 27, after "arg-gly-met-gly-met-gly-gly-gly" insert -- SEQ ID NO: 7 --.
Line 48, after "(3.1.1)" insert -- SEQ ID NO: 8 --.
Line 49, after "(3.1.2)" insert -- SEQ ID NO: 8 --.
Line 55, after "(3.2.1)" insert -- SEQ ID NO: 8 --.
Line 56, after "(3.2.2)" insert -- SEQ ID NO: 8 --.
Line 57, after "Solutions used" insert colon (:).
Line 64, after "arg-gly-met-gly-met-gly" insert -- SEQ ID NO: 8 --.

Column 15,
Line 2, after "arg-gly-met-gly-met-gly" insert -- SEQ ID NO: 8 --.
Line 17, after "$CONH_2$" insert -- SEQ ID NO: 8 --.
Line 19, after "gly-met-gly-met-gly" insert -- SEQ ID NO: 8 --.
Line 25, after "arg-gly-met-gly-met-gly" insert -- SEQ ID NO: 8 --.
Line 45, after "(4.1)" insert -- SEQ ID NO: 1 --.
Line 51, after "$CONH_2$" insert -- SEQ ID NO: 1 --.
Line 53, after "CONH2" insert -- SEQ ID NO: 1 --.

UNITED STATES PATENT AND TRADEMARK OFFICE
CERTIFICATE OF CORRECTION

PATENT NO. : 6,291,639 B1
DATED : September 18, 2001
INVENTOR(S) : Jurgen Conrad et al.

It is certified that error appears in the above-identified patent and that said Letters Patent is hereby corrected as shown below:

Column 16,
Line 27, "leu-asp-ile-trp-COOH" should read -- leu-asp-ile-ile-trp-COOH --.
Line 27, after "(6.1)" insert -- SEQ ID NO: 33 --.
Line 33, "ile-trp" should read -- ile-ile-trp --.
Line 33, after "trp-COOH" insert -- SEQ ID NO: 33 --.
Line 34, after "Solutions used" insert colon (:).
Line 42, after "COOH" insert -- SEQ ID NO: 33 --.
Line 53, after "COOH" insert -- SEQ ID NO: 33 --.
Line 56, after "COOH" insert -- SEQ ID NO: 33 --.

Column 17,
Line 3, between "-his-" and "-asp-" insert -- leu --.
Line 3, after "COOH" insert -- SEQ ID NO: 33 --.
Line 6, after "trp" insert -- SEQ ID NO: 33 --.
Line 12, after "-ile-ile-trp" insert -- SEQ ID NO: 33 --.
Line 36, after "ile-ile-trp" insert -- SEQ ID NO: 33 --.
Line 45, after "ile-ile-trp" insert -- SEQ ID NO: 33 --.
Line 55, after "ile-ile-trp" insert -- SEQ ID NO: 33 --.
Line 63, after "ile-ile-trp" insert -- SEQ ID NO: 33 --.

Column 43,
Line 11, "-qlv-" should read -- gly --.
Line 13, "arg-arq" should read -- arg-arg --.

Column 44,
Line 3, "encephaliins" should read -- encephalins --.
Line 41, after "amino groups" insert -- such as peptides, proteins, antibodies or their fragments, --.
Line 57, "encephaliins" should read -- encephalins --.

Column 45,
Line 1, after "amino groups" insert -- such as peptides, proteins, antibodies or their fragments, --.

Column 46,
Line 55, "Cyclo-" insert -- ( --.

Column 47,
Line 57, after "Cyclo-" insert -- ( --.

UNITED STATES PATENT AND TRADEMARK OFFICE
CERTIFICATE OF CORRECTION

PATENT NO.     : 6,291,639 B1
DATED          : September 18, 2001
INVENTOR(S)    : Jurgen Conrad et al.

It is certified that error appears in the above-identified patent and that said Letters Patent is hereby corrected as shown below:

Column 48,
Line 56, after "Cyclo-" insert -- ( --.

Column 49,
Line 57, after "Cyclo-" insert -- ( --.

Column 50,
Line 45, "gly-gly-gly-qly-" should read -- gly-gly-gly-gly --.

Signed and Sealed this

Fifteenth Day of July, 2003

JAMES E. ROGAN
*Director of the United States Patent and Trademark Office*

SEQUENCE LISTING (1) GENERAL INFORMATION:

(iii) NUMBER OF SEQUENCES:   35

(2) INFORMATION FOR SEQ ID NO:1:

(i) SEQUENCE CHARACTERISTICS:
        (A) LENGTH:       6 amino acids
        (B) TYPE:         amino acid
        (C) STRANDEDNESS: single
        (D) TOPOLOGY:     linear (ii) MOLECULE TYPE:    peptide (iii) HYPOTHETICAL:    no (iv) ANTI-SENSE:       no (v) FRAGMENT TYPE: internal (vi) ORIGINAL SOURCE:

(xi) SEQUENCE DESCRIPTION: SEQ ID NO: 1:

Glu Met Gly Asn Gly Glu
1               5

(2) INFORMATION FOR SEQ ID NO:2:

(i) SEQUENCE CHARACTERISTICS:
        (A) LENGTH:       6 amino acids
        (B) TYPE:         amino acid
        (C) STRANDEDNESS: single
        (D) TOPOLOGY:     linear (ii) MOLECULE TYPE:    peptide (iii) HYPOTHETICAL:    no (iv) ANTI-SENSE:       no (v) FRAGMENT TYPE: internal (vi) ORIGINAL SOURCE:

(xi) SEQUENCE DESCRIPTION: SEQ ID NO: 2:

Gly Gly Gly Gly Gly Met
1               5

(2) INFORMATION FOR SEQ ID NO:3:

(i) SEQUENCE CHARACTERISTICS:
        (A) LENGTH:       6 amino acids
        (B) TYPE:         amino acid
        (C) STRANDEDNESS: single
        (D) TOPOLOGY:     linear (ii) MOLECULE TYPE:    peptide (iii) HYPOTHETICAL:    no (iv) ANTI-SENSE:       no (v) FRAGMENT TYPE: internal (vi) ORIGINAL SOURCE:

(xi) SEQUENCE DESCRIPTION: SEQ ID NO: 3:

Met Gly Gly Gly Gly Met
1               5

(2) INFORMATION FOR SEQ ID NO:4:

(i) SEQUENCE CHARACTERISTICS:
        (A) LENGTH:        7 amino acids
        (B) TYPE:          amino acid
        (C) STRANDEDNESS:  single
        (D) TOPOLOGY:      linear (ii) MOLECULE TYPE:    peptide (iii) HYPOTHETICAL:    no (iv) ANTI-SENSE:       no (v) FRAGMENT TYPE: internal (vi) ORIGINAL SOURCE:

(xi) SEQUENCE DESCRIPTION: SEQ ID NO: 4:

Met Gly Met Gly His Gly His
1               5

(2) INFORMATION FOR SEQ ID NO:5:

(i) SEQUENCE CHARACTERISTICS:
        (A) LENGTH:        8 amino acids
        (B) TYPE:          amino acid
        (C) STRANDEDNESS:  single
        (D) TOPOLOGY:      linear (ii) MOLECULE TYPE:    peptide (iii) HYPOTHETICAL:    no (iv) ANTI-SENSE:       no (v) FRAGMENT TYPE: internal (vi) ORIGINAL SOURCE:

(xi) SEQUENCE DESCRIPTION: SEQ ID NO: 5:

Met Gly Met Gly Met Gly Met Gly
1               5

(2) INFORMATION FOR SEQ ID NO:6:

(i) SEQUENCE CHARACTERISTICS:
        (A) LENGTH:        8 amino acids
        (B) TYPE:          amino acid
        (C) STRANDEDNESS:  single
        (D) TOPOLOGY:      linear (ii) MOLECULE TYPE:    peptide (iii) HYPOTHETICAL:    no (iv) ANTI-SENSE:       no (v) FRAGMENT TYPE: internal (vi) ORIGINAL SOURCE:

(xi) SEQUENCE DESCRIPTION: SEQ ID NO: 6:

Gly Gly Met Gly Met Gly Gly Gly
1               5

(2) INFORMATION FOR SEQ ID NO:7:

(i) SEQUENCE CHARACTERISTICS:
        (A) LENGTH:        8 amino acids
        (B) TYPE:          amino acid
        (C) STRANDEDNESS:  single

```
        (D) TOPOLOGY:      linear (ii) MOLECULE TYPE:    peptide (iii) HYPOTHETICAL:     no (iv) ANTI-SENSE:       no (v) FRAGMENT TYPE: internal (vi) ORIGINAL SOURCE:

(xi) SEQUENCE DESCRIPTION: SEQ ID NO: 7:

Arg Gly Met Gly Met Gly Gly Gly
1               5

(2) INFORMATION FOR SEQ ID NO:8:

(i) SEQUENCE CHARACTERISTICS:
         (A) LENGTH:       6 amino acids
         (B) TYPE:         amino acid
         (C) STRANDEDNESS: single
         (D) TOPOLOGY:     linear (ii) MOLECULE TYPE:    peptide (iii) HYPOTHETICAL:     no (iv) ANTI-SENSE:       no (v) FRAGMENT TYPE: internal (vi) ORIGINAL SOURCE:

(xi) SEQUENCE DESCRIPTION: SEQ ID NO: 8:

Arg Gly Met Gly Met Gly
1               5

(2) INFORMATION FOR SEQ ID NO:9:

(i) SEQUENCE CHARACTERISTICS:
         (A) LENGTH:       6 amino acids
         (B) TYPE:         amino acid
         (C) STRANDEDNESS: single
         (D) TOPOLOGY:     linear (ii) MOLECULE TYPE:    peptide (iii) HYPOTHETICAL:     no (iv) ANTI-SENSE:       no (v) FRAGMENT TYPE: internal (vi) ORIGINAL SOURCE:

(xi) SEQUENCE DESCRIPTION: SEQ ID NO: 9:

Arg Arg Gly Gly Gly Glu
1               5

(2) INFORMATION FOR SEQ ID NO:10:

(i) SEQUENCE CHARACTERISTICS:
         (A) LENGTH:       6 amino acids
         (B) TYPE:         amino acid
         (C) STRANDEDNESS: single
         (D) TOPOLOGY:     linear (ii) MOLECULE TYPE:    peptide (iii) HYPOTHETICAL:     no (iv) ANTI-SENSE:       no
```

(v) FRAGMENT TYPE: internal (vi) ORIGINAL SOURCE:

(xi) SEQUENCE DESCRIPTION: SEQ ID NO: 10:

Arg Gly Gly Gly Gly Gly
1               5

(2) INFORMATION FOR SEQ ID NO:11:

(i) SEQUENCE CHARACTERISTICS:
            (A) LENGTH:       6 amino acids
            (B) TYPE:         amino acid
            (C) STRANDEDNESS: single
            (D) TOPOLOGY:     linear (ii) MOLECULE TYPE:       peptide (iii) HYPOTHETICAL:       no (iv) ANTI-SENSE:          no (v) FRAGMENT TYPE: internal (vi) ORIGINAL SOURCE:

(xi) SEQUENCE DESCRIPTION: SEQ ID NO: 11:

Met Gly Met Gly His Gly
1               5

(2) INFORMATION FOR SEQ ID NO:12:

(i) SEQUENCE CHARACTERISTICS:
            (A) LENGTH:       6 amino acids
            (B) TYPE:         amino acid
            (C) STRANDEDNESS: single
            (D) TOPOLOGY:     linear (ii) MOLECULE TYPE:       peptide (iii) HYPOTHETICAL:       no (iv) ANTI-SENSE:          no (v) FRAGMENT TYPE: internal (vi) ORIGINAL SOURCE:

(xi) SEQUENCE DESCRIPTION: SEQ ID NO: 12:

Ala Lys His Lys His His
1               5

(2) INFORMATION FOR SEQ ID NO:13:

(i) SEQUENCE CHARACTERISTICS:
            (A) LENGTH:       6 amino acids
            (B) TYPE:         amino acid
            (C) STRANDEDNESS: single
            (D) TOPOLOGY:     linear (ii) MOLECULE TYPE:       peptide (iii) HYPOTHETICAL:       no (iv) ANTI-SENSE:          no (v) FRAGMENT TYPE: internal (vi) ORIGINAL SOURCE:

(xi) SEQUENCE DESCRIPTION: SEQ ID NO: 13:

```
Gly Met Arg Met Gly Arg
1               5

(2) INFORMATION FOR SEQ ID NO:14:

(i) SEQUENCE CHARACTERISTICS:
        (A) LENGTH:       6 amino acids
        (B) TYPE:         amino acid
        (C) STRANDEDNESS: single
        (D) TOPOLOGY:     linear (ii) MOLECULE TYPE:      peptide (iii) HYPOTHETICAL:       no (iv) ANTI-SENSE:          no (v) FRAGMENT TYPE: internal (vi) ORIGINAL SOURCE:

(xi) SEQUENCE DESCRIPTION: SEQ ID NO: 14:

Gly Met Lys Met Gly Arg
1               5

(2) INFORMATION FOR SEQ ID NO:15:

(i) SEQUENCE CHARACTERISTICS:
        (A) LENGTH:       8 amino acids
        (B) TYPE:         amino acid
        (C) STRANDEDNESS: single
        (D) TOPOLOGY:     linear (ii) MOLECULE TYPE:      peptide (iii) HYPOTHETICAL:       no (iv) ANTI-SENSE:          no (v) FRAGMENT TYPE: internal (vi) ORIGINAL SOURCE:

(xi) SEQUENCE DESCRIPTION: SEQ ID NO: 15:

Gly Gly Met Arg Met Gly Gly Gly
1               5

(2) INFORMATION FOR SEQ ID NO:16:

(i) SEQUENCE CHARACTERISTICS:
        (A) LENGTH:       8 amino acids
        (B) TYPE:         amino acid
        (C) STRANDEDNESS: single
        (D) TOPOLOGY:     linear (ii) MOLECULE TYPE:      peptide (iii) HYPOTHETICAL:       no (iv) ANTI-SENSE:          no (v) FRAGMENT TYPE: internal (vi) ORIGINAL SOURCE:

(xi) SEQUENCE DESCRIPTION: SEQ ID NO: 16:

Gly Gly Met Lys Met Gly Gly Gly
1               5

(2) INFORMATION FOR SEQ ID NO:17:

(i) SEQUENCE CHARACTERISTICS:
```

```
            (A) LENGTH:         21 amino acids
            (B) TYPE:           amino acid
            (C) STRANDEDNESS:   single
            (D) TOPOLOGY:       linear (ii) MOLECULE TYPE:     peptide (iii) HYPOTHETICAL:      no (iv) ANTI-SENSE:        no (v) FRAGMENT TYPE: internal (vi) ORIGINAL SOURCE:

(xi) SEQUENCE DESCRIPTION: SEQ ID NO: 17:

Cys Ser Cys Ser Ser Leu Met Asp Lys Glu Cys Val Tyr Phe Cys His
1               5                   10                  15

Leu Asp Ile Ile Trp
            20

(2) INFORMATION FOR SEQ ID NO:18:

(i) SEQUENCE CHARACTERISTICS:
            (A) LENGTH:         21 amino acids
            (B) TYPE:           amino acid
            (C) STRANDEDNESS:   single
            (D) TOPOLOGY:       linear (ii) MOLECULE TYPE:     peptide (iii) HYPOTHETICAL:      no (iv) ANTI-SENSE:        no (v) FRAGMENT TYPE: internal (vi) ORIGINAL SOURCE:

(xi) SEQUENCE DESCRIPTION: SEQ ID NO: 18:

Cys Ser Cys Ser Ser Trp Leu Asp Lys Glu Cys Val Tyr Phe Cys His
1               5                   10                  15

Leu Asp Ile Ile Trp
            20

(2) INFORMATION FOR SEQ ID NO:19:

(i) SEQUENCE CHARACTERISTICS:
            (A) LENGTH:         21 amino acids
            (B) TYPE:           amino acid
            (C) STRANDEDNESS:   single
            (D) TOPOLOGY:       linear (ii) MOLECULE TYPE:     peptide (iii) HYPOTHETICAL:      no (iv) ANTI-SENSE:        no (v) FRAGMENT TYPE: internal (vi) ORIGINAL SOURCE:

(xi) SEQUENCE DESCRIPTION: SEQ ID NO: 19:

Cys Thr Cys Phe Thr Tyr Lys Asp Lys Glu Cys Val Tyr Tyr Cys His
1               5                   10                  15

Leu Asp Ile Ile Trp
            20

(2) INFORMATION FOR SEQ ID NO:20:
```

```
       (i) SEQUENCE CHARACTERISTICS:
           (A) LENGTH:        21 amino acids
           (B) TYPE:          amino acid
           (C) STRANDEDNESS:  single
           (D) TOPOLOGY:      linear (ii) MOLECULE TYPE:     peptide (iii) HYPOTHETICAL:      no (iv) ANTI-SENSE:        no (v) FRAGMENT TYPE: internal (vi) ORIGINAL SOURCE:

(xi) SEQUENCE DESCRIPTION: SEQ ID NO: 20:

Cys Ser Ala Ser Ser Leu Met Asp Lys Glu Ala Val Tyr Phe Cys His
1               5                   10                  15

Leu Asp Ile Ile Trp
            20

(2) INFORMATION FOR SEQ ID NO:21:

(i) SEQUENCE CHARACTERISTICS:
           (A) LENGTH:        21 amino acids
           (B) TYPE:          amino acid
           (C) STRANDEDNESS:  single
           (D) TOPOLOGY:      linear (ii) MOLECULE TYPE:     peptide (iii) HYPOTHETICAL:      no (iv) ANTI-SENSE:        no (v) FRAGMENT TYPE: internal (vi) ORIGINAL SOURCE:

(xi) SEQUENCE DESCRIPTION: SEQ ID NO: 21:

Cys Ser Cys Asn Ser Trp Leu Asp Lys Glu Cys Val Tyr Phe Cys His
1               5                   10                  15

Leu Asp Ile Ile Trp
            20

(2) INFORMATION FOR SEQ ID NO:22:

(i) SEQUENCE CHARACTERISTICS:
           (A) LENGTH:        21 amino acids
           (B) TYPE:          amino acid
           (C) STRANDEDNESS:  single
           (D) TOPOLOGY:      linear (ii) MOLECULE TYPE:     peptide (iii) HYPOTHETICAL:      no (iv) ANTI-SENSE:        no (v) FRAGMENT TYPE: internal (vi) ORIGINAL SOURCE:

(xi) SEQUENCE DESCRIPTION: SEQ ID NO: 22:

Cys Ser Cys Lys Asp Met Thr Asp Lys Glu Cys Leu Asn Phe Cys His
1               5                   10                  15

Gln Asp Val Ile Trp
            20
```

(2) INFORMATION FOR SEQ ID NO:23:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: no (iv) ANTI-SENSE: no (v) FRAGMENT TYPE: internal (vi) ORIGINAL SOURCE:

(xi) SEQUENCE DESCRIPTION: SEQ ID NO: 23:

```
Ala Ser Cys Ser Ser Leu Met Asp Lys Glu Cys Val Tyr Phe Ala His
1               5                  10                  15
Leu Asp Ile Ile Trp
            20
```

(2) INFORMATION FOR SEQ ID NO:24:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: no (iv) ANTI-SENSE: no (v) FRAGMENT TYPE: internal (vi) ORIGINAL SOURCE:

(xi) SEQUENCE DESCRIPTION: SEQ ID NO: 24:

```
Ala Ser His Ser Ser Leu Met Asp Lys Glu Ala Val Tyr Phe Ala His
1               5                  10                  15
Leu Asp Ile Ile Trp
            20
```

(2) INFORMATION FOR SEQ ID NO:25:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (iii) HYPOTHETICAL: no (iv) ANTI-SENSE: no (v) FRAGMENT TYPE: internal (vi) ORIGINAL SOURCE:

(xi) SEQUENCE DESCRIPTION: SEQ ID NO: 25:

```
Cys Ser Cys Ser Ser Trp Leu Asp Lys Glu Ala Val Tyr Phe Ala His
1               5                  10                  15
Leu Asp Ile Ile Trp
            20
```

(2) INFORMATION FOR SEQ ID NO:26:

(i) SEQUENCE CHARACTERISTICS:
        (A) LENGTH:      11 amino acids
        (B) TYPE:        amino acid
        (C) STRANDEDNESS: single
        (D) TOPOLOGY:    linear (ii) MOLECULE TYPE:     peptide (iii) HYPOTHETICAL:     no (iv) ANTI-SENSE:       no (v) FRAGMENT TYPE: internal (vi) ORIGINAL SOURCE:

(xi) SEQUENCE DESCRIPTION: SEQ ID NO: 26:

Cys Val Tyr Phe Cys His Leu Asp Ile Ile Trp
1           5                  10

(2) INFORMATION FOR SEQ ID NO:27:

(i) SEQUENCE CHARACTERISTICS:
        (A) LENGTH:      16 amino acids
        (B) TYPE:        amino acid
        (C) STRANDEDNESS: single
        (D) TOPOLOGY:    linear (ii) MOLECULE TYPE:     peptide (iii) HYPOTHETICAL:     no (iv) ANTI-SENSE:       no (v) FRAGMENT TYPE: internal (vi) ORIGINAL SOURCE:

(ix) FEATURE: N-acetyl leucine at amino acide No. 1.

(xi) SEQUENCE DESCRIPTION: SEQ ID NO: 27:

Leu Met Asp Lys Glu Ala Val Tyr Phe Ala His Leu Asp Ile Ile Trp
1           5                 10              15

(2) INFORMATION FOR SEQ ID NO:28:

(i) SEQUENCE CHARACTERISTICS:
        (A) LENGTH:      6 amino acids
        (B) TYPE:        amino acid
        (C) STRANDEDNESS: single
        (D) TOPOLOGY:    linear (ii) MOLECULE TYPE:     peptide (iii) HYPOTHETICAL:     no (iv) ANTI-SENSE:       no (v) FRAGMENT TYPE: internal (vi) ORIGINAL SOURCE:

(xi) SEQUENCE DESCRIPTION: SEQ ID NO: 28:

His Leu Asp Ile Ile Trp
1           5

(29) INFORMATION FOR SEQ ID NO:29:

(i) SEQUENCE CHARACTERISTICS:

(A) LENGTH:        5 amino acids
            (B) TYPE:          amino acid
            (C) STRANDEDNESS:  single
            (D) TOPOLOGY:      circular (ii) MOLECULE TYPE:     peptide (iii) HYPOTHETICAL:       no (iv) ANTI-SENSE:         no (v) FRAGMENT TYPE: internal (vi) ORIGINAL SOURCE:

(ix) FEATURE:   DTrp DAsp Pro DVal Leu (xi) SEQUENCE DESCRIPTION: SEQ ID NO: 29:

Xaa Xaa Pro Xaa Leu
1               5

(2) INFORMATION FOR SEQ ID NO:30:

(i) SEQUENCE CHARACTERISTICS:
            (A) LENGTH:        5 amino acids
            (B) TYPE:          amino acid
            (C) STRANDEDNESS:  single
            (D) TOPOLOGY:      circular (ii) MOLECULE TYPE:     peptide (iii) HYPOTHETICAL:       no (iv) ANTI-SENSE:         no (v) FRAGMENT TYPE: internal (vi) ORIGINAL SOURCE:

(ix) FEATURE:   cyclo DGlu Ala alloDIle Leu DTrp (xi) SEQUENCE DESCRIPTION: SEQ ID NO: 30:

Xaa Ala Xaa Leu Xaa
1               5

(2) INFORMATION FOR SEQ ID NO:31:

(i) SEQUENCE CHARACTERISTICS:
            (A) LENGTH:        786 base pairs
            (B) TYPE:          nucleic acid
            (C) STRANDEDNESS:  single
            (D) TOPOLOGY:      linear (ii) MOLECULE TYPE:     c DNA/protein (iii) HYPOTHETICAL:       no (iv) ANTI-SENSE:         no (v) FRAGMENT TYPE: internal (vi) ORIGINAL SOURCE:

(vii) IMMEDIATE SOURCE:    (B) clone/B4-F/C3

(xi) SEQUENCE DESCRIPTION: SEQ ID NO: 31:

```
ACT AGT CGA CAT GGC TTG GGT GTG GAA CTG CTA TTC CTG ATG GCA GCT        48
Thr Ser Arg His Gly Leu Gly Val Glu Leu Leu Phe Leu Met Ala Ala
1               5                   10                  15

GCC CAA AGT GTC CAA GCA CAG ATC CAG TTG GTG CAG TCT GGA CCT TAC        96
Ala Gln Ser Val Gln Ala Gln Ile Gln Leu Val Gln Ser Gly Pro Tyr
            20                  25                  30
```

```
CTG AAG AAG CCT GGA GAG ACT GTC AAG ATC TCC TGC AAG GCT TCT GGA         144
Leu Lys Lys Pro Gly Glu Thr Val Lys Ile Ser Cys Lys Ala Ser Gly
         35                  40                  45

TAT ACC TTC ACA TAC TAT GGA ATG AAC TGG GTG AAG CAG GCT CCA GGA         192
Tyr Thr Phe Thr Tyr Tyr Gly Met Asn Trp Val Lys Gln Ala Pro Gly
 50                  55                  60

AGG GGT TTA AAG TGG ATG GGC TTG ATA AAC ACC TAC ACT GGA GAG             237
Arg Gly Leu Lys Trp Met Gly Leu Ile Asn Thr Tyr Thr Gly Glu
 65                  70                  75

CCA ACA TAT GAT GAT GAC TTC ACG GGA CGG TTT GCC TTC TCT TTG GAA         285
Pro Thr Tyr Asp Asp Asp Phe Thr Gly Arg Phe Ala Phe Ser Leu Glu
 80                  85                  90                  95

ACC TCT GTC AGT ACT GCC TAT TTG CAG ATC AGC AAC CTC AAG AAT GAG         333
Thr Ser Val Ser Thr Ala Tyr Leu Gln Ile Ser Asn Leu Lys Asn Glu
                100                 105                 110

GAC ACG GCT ACA TAT TTC TGT TCA AGA GGG GGG GGT CAG GAC AGG             378
Asp Thr Ala Thr Tyr Phe Cys Ser Arg Gly Gly Gly Gln Asp Arg
             115                 120                 125

GGT TTT GAC TAC TGG GGC CAA GGC ACC ACT CTC ACA GTC TCC TCA GGA         426
Gly Phe Asp Tyr Trp Gly Gln Gly Thr Thr Leu Thr Val Ser Ser Gly
         130                 135                 140

GGC GGT GGC TCG GGA GGT GGC GGC TCG GGT GGC GGC GGC TCT GAC             471
Gly Gly Gly Ser Gly Gly Gly Gly Ser Gly Gly Gly Gly Ser Asp
         145                 150                 155

ATT CAG CTG ACC CAG TCT CCA GCA ATC ATG TCT GCA TCT CCA GGG GAG         519
Ile Gln Leu Thr Gln Ser Pro Ala Ile Met Ser Ala Ser Pro Gly Glu
             160                 165                 170

AAG GTC ACC ATG ACC TGC AGT GCC AGC TCA AGT GTA AGT TAC ATG CAC         567
Lys Val Thr Met Thr Cys Ser Ala Ser Ser Ser Val Ser Tyr Met His
 175                 180                 185

TGG TAC CAG CAG AAG TCA GGC ACC TCC CCC AAA AGA TGG ATT TAT             612
Trp Tyr Gln Gln Lys Ser Gly Thr Ser Pro Lys Arg Trp Ile Tyr
190                 195                 200

GAC ACA TCC AAA CTG GCT TCT GGA GTC CCT GCT CGC TTC AGT GGC AGT         660
Asp Thr Ser Lys Leu Ala Ser Gly Val Pro Ala Arg Phe Ser Gly Ser
205                 210                 215                 220

GGG TCT GGG ACC TCT TAC TCT CTC ACA ATC AGC ACC ATG GAG GCT GAA         708
Gly Ser Gly Thr Ser Tyr Ser Leu Thr Ile Ser Thr Met Glu Ala Glu
             225                 230                 235

GAT GCT GCC ACT TAT TAC TGC CAG CAG TGG ACT AAT AAC CCG TAC ACG         756
Asp Ala Ala Thr Tyr Tyr Cys Gln Gln Trp Thr Asn Asn Pro Tyr Thr
         240                 245                 250

TTC GGA GGG GGG ACC AAG CTG GAG CTG AAA                                 786
Phe Gly Gly Gly Thr Lys Leu Glu Leu Lys
         255                 260

(2) INFORMATION FOR SEQ ID NO:32:

(i) SEQUENCE CHARACTERISTICS:
        (A) LENGTH:       17 amino acids
        (B) TYPE:         amino acid
        (C) STRANDEDNESS: single
        (D) TOPOLOGY:     linear (ii) MOLECULE TYPE:    peptide (iii) HYPOTHETICAL:     no (iv) ANTI-SENSE:       no (v) FRAGMENT TYPE: internal (vi) ORIGINAL SOURCE:
```

(xi) SEQUENCE DESCRIPTION: SEQ ID NO: 32:

Glu Met Gly Asn Gly Glu Cys Val Tyr Phe Cys His Leu Asp Ile Ile Trp
1               5                   10                  15

(2) INFORMATION FOR SEQ ID NO:33:

(i) SEQUENCE CHARACTERISTICS:
        (A) LENGTH:       17 amino acids
        (B) TYPE:         amino acid
        (C) STRANDEDNESS: single
        (D) TOPOLOGY:     linear (ii) MOLECULE TYPE:   peptide (iii) HYPOTHETICAL:    no (iv) ANTI-SENSE:      no (v) FRAGMENT TYPE: internal (vi) ORIGINAL SOURCE:

(xi) SEQUENCE DESCRIPTION: SEQ ID NO: 33:

Glu Met Gly Asn Gly Glu Cys Val Tyr Phe Cys His Leu Asp Ile Ile Trp
1               5                   10                  15

(2) INFORMATION FOR SEQ ID NO:34:

(i) SEQUENCE CHARACTERISTICS:
        (A) LENGTH:       15 amino acids
        (B) TYPE:         amino acid
        (C) STRANDEDNESS: single
        (D) TOPOLOGY:     linear (ii) MOLECULE TYPE:   peptide (iii) HYPOTHETICAL:    no (iv) ANTI-SENSE:      no (v) FRAGMENT TYPE: internal (vi) ORIGINAL SOURCE:

(xi) SEQUENCE DESCRIPTION: SEQ ID NO: 34:

Gly Gly Gly Gly Ser Gly Gly Gly Gly Ser Gly Gly Gly Gly Ser
1               5                   10                  15

(2) INFORMATION FOR SEQ ID NO:35:

(i) SEQUENCE CHARACTERISTICS:
        (A) LENGTH:       8 amino acids
        (B) TYPE:         amino acid
        (C) STRANDEDNESS: single
        (D) TOPOLOGY:     linear (ii) MOLECULE TYPE:   peptide (iii) HYPOTHETICAL:    no (iv) ANTI-SENSE:      no (v) FRAGMENT TYPE: internal (vi) ORIGINAL SOURCE:

(xi) SEQUENCE DESCRIPTION: SEQ ID NO: 35:

Pro Pro Met Gly Met Gly His Gly
1               5